US012089902B2

(12) United States Patent
Alexandroni et al.

(10) Patent No.: US 12,089,902 B2
(45) Date of Patent: Sep. 17, 2024

(54) CONE BEAM AND 3D FLUOROSCOPE LUNG NAVIGATION

(71) Applicant: Covidien LP, Mansfield, MA (US)

(72) Inventors: Guy Alexandroni, Haifa (IL); Oren P. Weingarten, Hod-Hasharon (IL); Evgeni Kopel, Barkan (IL); Ariel Birenbaum, Raanana (IL)

(73) Assignee: Coviden LP, Mansfield, MA (US)

( * ) Notice: Subject to any disclaimer, the term of this patent is extended or adjusted under 35 U.S.C. 154(b) by 863 days.

(21) Appl. No.: 16/909,721

(22) Filed: Jun. 23, 2020

(65) Prior Publication Data
US 2021/0030482 A1 Feb. 4, 2021

Related U.S. Application Data

(60) Provisional application No. 62/880,489, filed on Jul. 30, 2019.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/066* (2013.01); *A61B 34/10* (2016.02); *A61B 34/25* (2016.02);
(Continued)

(58) Field of Classification Search
CPC ......... A61B 34/20; A61B 5/066; A61B 34/10; A61B 34/25; A61B 6/032; A61B 6/12; A61B 6/541; A61B 2034/105; A61B 2034/107; A61B 2034/2051; A61B 2090/376; A61B 2090/3764; A61B 6/4441; A61B 6/5205; A61B 6/465; A61B 6/466; A61B 6/487; A61B 2090/3762; A61B 90/37; A61B 18/1492; A61B 2017/00809; A61B 2018/00577; A61B 2034/2061; A61B 2034/2072; A61B 2090/363;
(Continued)

(56) References Cited

U.S. PATENT DOCUMENTS 1,576,781 A  3/1926 Philips
1,735,726 A  11/1929 Bornhardt
(Continued)

FOREIGN PATENT DOCUMENTS

BR  0013237 A  7/2003
BR  0116004 A  6/2004
(Continued)

OTHER PUBLICATIONS

Extended European Search Report issued in European Patent Application No. 20188309.7 dated Mar. 31, 2021.
(Continued)

*Primary Examiner* — Joel Lamprecht
(74) *Attorney, Agent, or Firm* — Weber Rosselli & Cannon LLP

(57) ABSTRACT

A method and system for reducing divergence between computed tomography images and a patient using three-dimensional reconstructions. The method utilizes cone beam imaging or three-dimensional fluoroscopy to supplement or supplant pre-operative computed tomography imaging.

10 Claims, 11 Drawing Sheets

(51) Int. Cl.
  *A61B 34/00* (2016.01)
  *A61B 34/10* (2016.01)
  *G06T 7/30* (2017.01)
  *A61B 6/00* (2006.01)
  *A61B 6/03* (2006.01)
  *A61B 6/12* (2006.01)
  *A61B 90/00* (2016.01)

(52) U.S. Cl.
  CPC .............. *G06T 7/30* (2017.01); *A61B 6/032* (2013.01); *A61B 6/12* (2013.01); *A61B 6/541* (2013.01); *A61B 2034/105* (2016.02); *A61B 2034/107* (2016.02); *A61B 2034/2051* (2016.02); *A61B 2090/376* (2016.02); *A61B 2090/3764* (2016.02)

(58) Field of Classification Search
  CPC . A61B 2090/364; A61B 6/4085; A61B 6/485; G06T 7/30
  See application file for complete search history.

(56) References Cited

U.S. PATENT DOCUMENTS

| | | | |
|---|---|---|---|
| 2,407,845 | A | 9/1946 | Nemeyer |
| 2,650,588 | A | 9/1953 | Drew |
| 2,697,433 | A | 12/1954 | Zehnder |
| 3,016,899 | A | 1/1962 | Stenvall |
| 3,017,887 | A | 1/1962 | Heyer |
| 3,061,936 | A | 11/1962 | De |
| 3,073,310 | A | 1/1963 | Mocarski |
| 3,109,588 | A | 11/1963 | Polhemus et al. |
| 3,121,228 | A | 2/1964 | Kalmus |
| 3,294,083 | A | 12/1966 | Alderson |
| 3,367,326 | A | 2/1968 | Frazier |
| 3,439,256 | A | 4/1969 | Robert |
| 3,519,436 | A | 7/1970 | Bauer et al. |
| 3,577,160 | A | 5/1971 | White |
| 3,600,625 | A | 8/1971 | Asahide et al. |
| 3,605,725 | A | 9/1971 | Bentov |
| 3,614,950 | A | 10/1971 | Graham |
| 3,644,825 | A | 2/1972 | Davis et al. |
| 3,674,014 | A | 7/1972 | Hans |
| 3,702,935 | A | 11/1972 | Carey et al. |
| 3,704,707 | A | 12/1972 | Halloran |
| 3,821,469 | A | 6/1974 | Whetstone et al. |
| 3,822,697 | A | 7/1974 | Komiya |
| 3,868,565 | A | 2/1975 | Kuipers |
| 3,941,127 | A | 3/1976 | Froning |
| 3,983,474 | A | 9/1976 | Kuipers |
| 4,017,858 | A | 4/1977 | Kuipers |
| 4,037,592 | A | 7/1977 | Kronner |
| 4,052,620 | A | 10/1977 | Brunnett |
| 4,054,881 | A | 10/1977 | Raab |
| 4,117,337 | A | 9/1978 | Staats |
| 4,135,184 | A | 1/1979 | Pruzick |
| 4,173,228 | A | 11/1979 | Childress et al. |
| 4,182,312 | A | 1/1980 | Mushabac |
| 4,202,349 | A | 5/1980 | Jones |
| 4,228,799 | A | 10/1980 | Anichkov et al. |
| 4,249,167 | A | 2/1981 | Purinton et al. |
| 4,256,112 | A | 3/1981 | David et al. |
| 4,262,306 | A | 4/1981 | Renner |
| 4,287,809 | A | 9/1981 | Egli et al. |
| 4,298,874 | A | 11/1981 | Kuipers |
| 4,308,530 | A | 12/1981 | Kip et al. |
| 4,314,251 | A | 2/1982 | Raab |
| 4,317,078 | A | 2/1982 | Weed et al. |
| 4,319,136 | A | 3/1982 | Randolph |
| 4,328,548 | A | 5/1982 | Crow et al. |
| 4,328,813 | A | 5/1982 | Ray |
| 4,339,953 | A | 7/1982 | Iwasaki |
| 4,341,220 | A | 7/1982 | Perry |
| 4,341,385 | A | 7/1982 | Doyle et al. |
| 4,346,384 | A | 8/1982 | Raab |
| 4,358,856 | A | 11/1982 | Stivender et al. |
| 4,368,536 | A | 1/1983 | Pfeiler |
| 4,394,831 | A | 7/1983 | Egli et al. |
| 4,396,885 | A | 8/1983 | Constant |
| 4,396,945 | A | 8/1983 | Dimatteo et al. |
| 4,403,321 | A | 9/1983 | Krueger |
| 4,418,422 | A | 11/1983 | Richter et al. |
| 4,419,012 | A | 12/1983 | Stephenson et al. |
| 4,422,041 | A | 12/1983 | Lienau |
| 4,425,511 | A | 1/1984 | Brosh |
| 4,431,005 | A | 2/1984 | Mccormick |
| 4,447,224 | A | 5/1984 | Decant, Jr. et al. |
| 4,447,462 | A | 5/1984 | Tafuri et al. |
| 4,485,815 | A | 12/1984 | Amplatz et al. |
| 4,506,676 | A | 3/1985 | Duska |
| 4,543,959 | A | 10/1985 | Sepponen |
| 4,548,208 | A | 10/1985 | Niemi |
| 4,571,834 | A | 2/1986 | Fraser et al. |
| 4,572,198 | A | 2/1986 | Codrington |
| 4,583,538 | A | 4/1986 | Onik et al. |
| 4,584,577 | A | 4/1986 | Temple |
| 4,586,491 | A | 5/1986 | Carpenter |
| 4,587,975 | A | 5/1986 | Salo et al. |
| 4,608,977 | A | 9/1986 | Brown |
| 4,613,866 | A | 9/1986 | Blood |
| 4,617,925 | A | 10/1986 | Laitinen |
| 4,618,978 | A | 10/1986 | Cosman |
| 4,621,628 | A | 11/1986 | Brudermann |
| 4,625,718 | A | 12/1986 | Olerud et al. |
| 4,638,798 | A | 1/1987 | Hunter et al. |
| 4,642,786 | A | 2/1987 | Hansen |
| 4,645,343 | A | 2/1987 | Stockdale et al. |
| 4,649,504 | A | 3/1987 | Krouglicof et al. |
| 4,651,732 | A | 3/1987 | Frederick |
| 4,653,509 | A | 3/1987 | Oloff et al. |
| 4,659,971 | A | 4/1987 | Suzuki et al. |
| 4,660,970 | A | 4/1987 | Ferrano |
| 4,673,352 | A | 6/1987 | Hansen |
| 4,686,695 | A | 8/1987 | Macovski |
| 4,688,037 | A | 8/1987 | Krieg |
| 4,696,544 | A | 9/1987 | Costella |
| 4,697,595 | A | 10/1987 | Breyer et al. |
| 4,701,049 | A | 10/1987 | Beckman et al. |
| 4,704,602 | A | 11/1987 | Asbrink |
| 4,705,395 | A | 11/1987 | Hageniers |
| 4,705,401 | A | 11/1987 | Addleman et al. |
| 4,706,665 | A | 11/1987 | Gouda |
| 4,709,156 | A | 11/1987 | Murphy et al. |
| 4,710,708 | A | 12/1987 | Rorden et al. |
| 4,719,419 | A | 1/1988 | Dawley |
| 4,722,056 | A | 1/1988 | Roberts et al. |
| 4,722,336 | A | 2/1988 | Kim et al. |
| 4,723,544 | A | 2/1988 | Moore et al. |
| 4,726,355 | A | 2/1988 | Okada |
| 4,727,565 | A | 2/1988 | Ericson |
| 4,733,969 | A | 3/1988 | Case et al. |
| 4,737,032 | A | 4/1988 | Addleman et al. |
| 4,737,794 | A | 4/1988 | Jones |
| 4,737,921 | A | 4/1988 | Goldwasser et al. |
| 4,742,356 | A | 5/1988 | Kuipers |
| 4,742,815 | A | 5/1988 | Ninan et al. |
| 4,743,770 | A | 5/1988 | Lee |
| 4,743,771 | A | 5/1988 | Sacks et al. |
| 4,745,290 | A | 5/1988 | Frankel et al. |
| 4,750,487 | A | 6/1988 | Zanetti |
| 4,753,528 | A | 6/1988 | Hines et al. |
| 4,761,072 | A | 8/1988 | Pryor |
| 4,764,016 | A | 8/1988 | Johansson |
| 4,771,787 | A | 9/1988 | Wurster et al. |
| 4,779,212 | A | 10/1988 | Levy |
| 4,782,239 | A | 11/1988 | Hirose et al. |
| 4,784,117 | A | 11/1988 | Miyazaki |
| 4,788,481 | A | 11/1988 | Niwa |
| 4,791,934 | A | 12/1988 | Brunnett |
| 4,793,355 | A | 12/1988 | Crum et al. |
| 4,794,262 | A | 12/1988 | Sato et al. |
| 4,797,907 | A | 1/1989 | Anderton |
| 4,803,976 | A | 2/1989 | Frigg et al. |
| 4,804,261 | A | 2/1989 | Kirschen |

(56) References Cited

U.S. PATENT DOCUMENTS

| | | |
|---|---|---|
| 4,805,615 A | 2/1989 | Carol |
| 4,809,694 A | 3/1989 | Ferrara |
| 4,821,200 A | 4/1989 | Deberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,250 A | 5/1989 | Rotier |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,912 A | 8/1990 | Langberg |
| 4,945,914 A | 8/1990 | Allen |
| 4,951,653 A | 8/1990 | Fry et al. |
| 4,955,891 A | 9/1990 | Carol |
| 4,961,422 A | 10/1990 | Alexander et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,047 A | 5/1991 | Schwab |
| 5,013,317 A | 5/1991 | Dean et al. |
| 5,016,639 A | 5/1991 | Allen |
| 5,017,139 A | 5/1991 | Mushabac |
| 5,023,102 A | 6/1991 | Given, Jr. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,070,462 A | 12/1991 | Chau |
| 5,078,140 A | 1/1992 | Kwoh |
| 5,079,699 A | 1/1992 | Tuy et al. |
| 5,082,286 A | 1/1992 | Ryan et al. |
| 5,086,401 A | 2/1992 | Glassman et al. |
| 5,088,928 A | 2/1992 | Chan |
| 5,094,241 A | 3/1992 | Allen |
| 5,097,839 A | 3/1992 | Allen |
| 5,098,426 A | 3/1992 | Alfred et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,127,408 A | 7/1992 | Parsons et al. |
| 5,129,654 A | 7/1992 | Bogner |
| 5,142,930 A | 9/1992 | Allen et al. |
| 5,143,076 A | 9/1992 | Hardy et al. |
| 5,152,277 A | 10/1992 | Honda et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,130 A | 1/1993 | Kaiya |
| 5,178,164 A | 1/1993 | Allen |
| 5,178,621 A | 1/1993 | Cook et al. |
| 5,186,174 A | 2/1993 | Schloendorff et al. |
| 5,187,475 A | 2/1993 | Wagener et al. |
| 5,188,126 A | 2/1993 | Fabian et al. |
| 5,188,368 A | 2/1993 | Ryan |
| 5,190,059 A | 3/1993 | Fabian et al. |
| 5,190,285 A | 3/1993 | Levy et al. |
| 5,193,106 A | 3/1993 | Desena |
| 5,196,928 A | 3/1993 | Karasawa et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,203,337 A | 4/1993 | Feldman |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,262,722 A | 11/1993 | Hedengren et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,307,816 A | 5/1994 | Hashimoto et al. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,327,889 A | 7/1994 | Imran |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,347,289 A | 9/1994 | Elhardt |
| 5,353,795 A | 10/1994 | Souza et al. |
| 5,353,800 A | 10/1994 | Pohndorf et al. |
| 5,353,807 A | 10/1994 | Demarco |

(56) References Cited

U.S. PATENT DOCUMENTS

| | | |
|---|---|---|
| 5,357,253 A | 10/1994 | Van et al. |
| 5,359,417 A | 10/1994 | Mueller et al. |
| 5,368,030 A | 11/1994 | Zinreich et al. |
| 5,371,778 A | 12/1994 | Yanof et al. |
| 5,375,596 A | 12/1994 | Twiss et al. |
| 5,376,795 A | 12/1994 | Hasegawa et al. |
| 5,377,678 A | 1/1995 | Dumoulin et al. |
| 5,383,454 A | 1/1995 | Bucholz et al. |
| 5,383,852 A | 1/1995 | Stevens-Wright et al. |
| 5,385,146 A | 1/1995 | Goldreyer |
| 5,385,148 A | 1/1995 | Lesh et al. |
| 5,386,828 A | 2/1995 | Owens et al. |
| 5,389,073 A | 2/1995 | Imran |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,321 A | 3/1995 | Houser et al. |
| 5,397,329 A | 3/1995 | Allen |
| 5,398,684 A | 3/1995 | Hardy |
| 5,398,691 A | 3/1995 | Martin et al. |
| 5,399,146 A | 3/1995 | Nowacki et al. |
| 5,400,384 A | 3/1995 | Fernandes et al. |
| 5,400,771 A | 3/1995 | Pirak et al. |
| 5,402,801 A | 4/1995 | Taylor |
| 5,405,346 A | 4/1995 | Grundy et al. |
| 5,408,409 A | 4/1995 | Glassman et al. |
| 5,409,000 A | 4/1995 | Imran |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'farrell et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| 5,435,573 A | 7/1995 | Oakford |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,447,156 A | 9/1995 | Dumoulin et al. |
| 5,448,610 A | 9/1995 | Yamamoto et al. |
| 5,453,686 A | 9/1995 | Anderson |
| 5,456,254 A | 10/1995 | Pietroski et al. |
| 5,456,664 A | 10/1995 | Heinzelman et al. |
| 5,456,689 A | 10/1995 | Kresch et al. |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,472,441 A | 12/1995 | Edwards et al. |
| 5,476,100 A | 12/1995 | Galel |
| 5,476,495 A | 12/1995 | Kordis et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,492,131 A | 2/1996 | Galel |
| 5,492,713 A | 2/1996 | Sommermeyer |
| 5,493,517 A | 2/1996 | Frazier |
| 5,494,034 A | 2/1996 | Schloendorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,515,853 A | 5/1996 | Smith et al. |
| 5,517,990 A | 5/1996 | Kalfas et al. |
| 5,520,059 A | 5/1996 | Garshelis |
| 5,522,814 A | 6/1996 | Bernaz |
| 5,522,815 A | 6/1996 | Durgin, Jr. et al. |
| 5,531,227 A | 7/1996 | Bret |
| 5,531,520 A | 7/1996 | Grimson et al. |
| 5,531,686 A | 7/1996 | Lundquist et al. |
| 5,542,938 A | 8/1996 | Avellanet et al. |
| 5,543,951 A | 8/1996 | Moehrmann |
| 5,545,200 A | 8/1996 | West et al. |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Michael et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-Haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover et al. |
| 5,588,033 A | 12/1996 | Yeung |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,599,305 A | 2/1997 | Hermann et al. |
| 5,600,330 A | 2/1997 | Blood |
| 5,603,318 A | 2/1997 | Heilbrun et al. |
| 5,606,975 A | 3/1997 | Liang et al. |
| 5,611,025 A | 3/1997 | Lorensen et al. |
| 5,617,462 A | 4/1997 | Bruce |
| 5,617,857 A | 4/1997 | Chader et al. |
| 5,619,261 A | 4/1997 | Larry |
| 5,620,734 A | 4/1997 | Wesdorp et al. |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,634 A | 6/1997 | Kordis et al. |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Larry et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,646,525 A | 7/1997 | Gilboa |
| 5,647,361 A | 7/1997 | Damadian |
| 5,651,047 A | 7/1997 | Moorman et al. |
| 5,660,856 A | 8/1997 | Adler-Moore et al. |
| 5,662,108 A | 9/1997 | Budd et al. |
| 5,662,111 A | 9/1997 | Cosman |
| 5,664,001 A | 9/1997 | Tachibana et al. |
| 5,668,844 A | 9/1997 | Webber |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |

(56) References Cited

U.S. PATENT DOCUMENTS

| | | |
|---|---|---|
| 5,695,501 A | 12/1997 | Carol et al. |
| 5,696,500 A | 12/1997 | Diem |
| 5,697,377 A | 12/1997 | Wittkampf |
| 5,699,799 A | 12/1997 | Xu et al. |
| 5,701,898 A | 12/1997 | Adam et al. |
| 5,702,406 A | 12/1997 | Vilsmeier et al. |
| 5,704,361 A | 1/1998 | Seward et al. |
| 5,711,299 A | 1/1998 | Manwaring et al. |
| 5,713,369 A | 2/1998 | Tao et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Michael et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,741,320 A | 4/1998 | Thornton et al. |
| 5,742,394 A | 4/1998 | Hansen |
| 5,744,802 A | 4/1998 | Muehllehner et al. |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,518 A | 5/1998 | Mcgee et al. |
| 5,755,725 A | 5/1998 | Druais |
| 5,758,667 A | 6/1998 | Slettenmark |
| 5,760,335 A | 6/1998 | Gilboa |
| 5,762,064 A | 6/1998 | Polvani |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,050 A | 7/1998 | Chen et al. |
| 5,776,064 A | 7/1998 | Kalfas et al. |
| 5,782,762 A | 7/1998 | Vining |
| 5,782,765 A | 7/1998 | Jonkman |
| 5,782,828 A | 7/1998 | Chen et al. |
| 5,787,886 A | 8/1998 | Kelly et al. |
| 5,792,055 A | 8/1998 | Mckinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'farrell et al. |
| 5,803,084 A | 9/1998 | Olson |
| 5,803,089 A | 9/1998 | Ferre et al. |
| 5,807,252 A | 9/1998 | Hassfeld et al. |
| 5,810,007 A | 9/1998 | Holupka et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,837,001 A | 11/1998 | Mackey |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,853,327 A | 12/1998 | Gilboa |
| 5,857,997 A | 1/1999 | Cimino et al. |
| 5,865,726 A | 2/1999 | Katsurada et al. |
| 5,865,846 A | 2/1999 | Bryan et al. |
| 5,868,673 A | 2/1999 | Vesely |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,871,523 A | 2/1999 | Fleischman et al. |
| 5,873,822 A | 2/1999 | Ferre et al. |
| 5,881,124 A | 3/1999 | Giger et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,030 A | 4/1999 | Johnson et al. |
| 5,891,034 A | 4/1999 | Bucholz |
| 5,891,134 A | 4/1999 | Goble et al. |
| 5,891,157 A | 4/1999 | Day et al. |
| 5,893,885 A | 4/1999 | Webster, Jr. |
| 5,899,860 A | 5/1999 | Pfeiffer et al. |
| 5,902,239 A | 5/1999 | Buurman |
| 5,902,324 A | 5/1999 | Thompson et al. |
| 5,904,691 A | 5/1999 | Barnett et al. |
| 5,907,395 A | 5/1999 | Schulz et al. |
| 5,909,476 A | 6/1999 | Wang et al. |
| 5,913,820 A | 6/1999 | Bladen et al. |
| 5,916,210 A | 6/1999 | Winston |
| 5,919,147 A | 7/1999 | Jain |
| 5,919,188 A | 7/1999 | Shearon et al. |
| 5,920,319 A | 7/1999 | Vining et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,930,329 A | 7/1999 | Navab |
| 5,935,160 A | 8/1999 | Auricchio et al. |
| 5,938,585 A | 8/1999 | Donofrio |
| 5,938,602 A | 8/1999 | Lloyd |
| 5,938,603 A | 8/1999 | Ponzi |
| 5,938,694 A | 8/1999 | Jaraczewski et al. |
| 5,941,251 A | 8/1999 | Panescu et al. |
| 5,944,023 A | 8/1999 | Johnson et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,461 A | 9/1999 | Nyo et al. |
| 5,951,475 A | 9/1999 | Gueziec et al. |
| 5,951,571 A | 9/1999 | Audette |
| 5,954,647 A | 9/1999 | Bova et al. |
| 5,954,649 A | 9/1999 | Chia et al. |
| 5,954,796 A | 9/1999 | Mccarty et al. |
| 5,957,844 A | 9/1999 | Dekel et al. |
| 5,966,090 A | 10/1999 | Mcewan |
| 5,967,980 A | 10/1999 | Ferre et al. |
| 5,967,982 A | 10/1999 | Barnett |
| 5,968,047 A | 10/1999 | Reed |
| 5,971,767 A | 10/1999 | Kaufman et al. |
| 5,971,997 A | 10/1999 | Guthrie et al. |
| 5,976,127 A | 11/1999 | Lax |
| 5,976,156 A | 11/1999 | Taylor et al. |
| 5,980,504 A | 11/1999 | Sharkey et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |

(56) References Cited

U.S. PATENT DOCUMENTS

| | | |
|---|---|---|
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Brug et al. |
| 6,013,087 A | 1/2000 | Adams et al. |
| 6,014,580 A | 1/2000 | Blume et al. |
| 6,016,439 A | 1/2000 | Acker |
| 6,019,724 A | 2/2000 | Gronningsaeter et al. |
| 6,019,725 A | 2/2000 | Vesely et al. |
| 6,019,728 A | 2/2000 | Iwata et al. |
| 6,022,578 A | 2/2000 | Miller |
| 6,024,695 A | 2/2000 | Taylor et al. |
| 6,024,739 A | 2/2000 | Ponzi et al. |
| 6,032,675 A | 3/2000 | Rubinsky |
| 6,035,229 A | 3/2000 | Silverstein et al. |
| 6,047,080 A | 4/2000 | Chen et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,064,390 A | 5/2000 | Sagar et al. |
| 6,071,288 A | 6/2000 | Carol et al. |
| 6,073,043 A | 6/2000 | Schneider |
| 6,076,008 A | 6/2000 | Bucholz |
| 6,077,257 A | 6/2000 | Edwards et al. |
| 6,083,162 A | 7/2000 | Vining |
| 6,096,036 A | 8/2000 | Bowe et al. |
| 6,096,050 A | 8/2000 | Audette |
| 6,104,294 A | 8/2000 | Andersson et al. |
| 6,104,944 A | 8/2000 | Martinelli |
| 6,106,517 A | 8/2000 | Zupkas |
| 6,112,111 A | 8/2000 | Glantz |
| 6,115,626 A | 9/2000 | Whayne et al. |
| 6,117,476 A | 9/2000 | Eger et al. |
| 6,118,845 A | 9/2000 | Simon et al. |
| 6,122,538 A | 9/2000 | Sliwa, Jr. et al. |
| 6,122,541 A | 9/2000 | Cosman et al. |
| 6,123,979 A | 9/2000 | Hepburn et al. |
| 6,131,396 A | 10/2000 | Duerr et al. |
| 6,138,045 A | 10/2000 | Kupinski et al. |
| 6,139,183 A | 10/2000 | Graumann |
| 6,147,480 A | 11/2000 | Osadchy et al. |
| 6,149,592 A | 11/2000 | Yanof et al. |
| 6,151,404 A | 11/2000 | Pieper |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,179,809 B1 | 1/2001 | Khairkhahan et al. |
| 6,181,348 B1 | 1/2001 | Geiger |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,208,884 B1 | 3/2001 | Kumar et al. |
| 6,210,362 B1 | 4/2001 | Ponzi |
| 6,211,666 B1 | 4/2001 | Acker |
| 6,213,995 B1 | 4/2001 | Steen et al. |
| 6,213,998 B1 | 4/2001 | Shen et al. |
| 6,216,027 B1 | 4/2001 | Parker et al. |
| 6,216,029 B1 | 4/2001 | Paltieli |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,245,020 B1 | 6/2001 | Moore et al. |
| 6,246,231 B1 | 6/2001 | Ashe |
| 6,246,784 B1 | 6/2001 | Summers et al. |
| 6,246,898 B1 | 6/2001 | Vesely et al. |
| 6,246,899 B1 | 6/2001 | Chia et al. |
| 6,248,074 B1 | 6/2001 | Ohno et al. |
| 6,253,770 B1 | 7/2001 | Acker et al. |
| 6,259,942 B1 | 7/2001 | Westermann et al. |
| 6,264,654 B1 | 7/2001 | Swartz et al. |
| 6,266,551 B1 | 7/2001 | Osadchy et al. |
| 6,272,371 B1 | 8/2001 | Shlomo |
| 6,273,896 B1 | 8/2001 | Franck et al. |
| 6,285,902 B1 | 9/2001 | Kienzle et al. |
| 6,289,235 B1 | 9/2001 | Webber et al. |
| 6,298,262 B1 | 10/2001 | Franck et al. |
| 6,304,769 B1 | 10/2001 | Arenson et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,331,116 B1 | 12/2001 | Kaufman et al. |
| 6,331,156 B1 | 12/2001 | Haefele et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,346,940 B1 | 2/2002 | Fukunaga |
| 6,351,513 B1 | 2/2002 | Bani-Hashemi et al. |
| 6,351,659 B1 | 2/2002 | Vilsmeier |
| 6,366,799 B1 | 4/2002 | Acker et al. |
| 6,366,800 B1 | 4/2002 | Vining et al. |
| 6,373,240 B1 | 4/2002 | Govari |
| 6,373,916 B1 | 4/2002 | Inoue et al. |
| 6,380,732 B1 | 4/2002 | Gilboa |
| 6,381,485 B1 | 4/2002 | Hunter et al. |
| 6,383,144 B1 | 5/2002 | Mooney et al. |
| 6,387,092 B1 | 5/2002 | Burnside et al. |
| 6,405,072 B1 | 6/2002 | Cosman |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,466,815 B1 | 10/2002 | Saito et al. |
| 6,468,265 B1 | 10/2002 | Evans et al. |
| 6,470,207 B1 | 10/2002 | Simon et al. |
| 6,473,634 B1 | 10/2002 | Barni |
| 6,473,635 B1 | 10/2002 | Rasche |
| 6,474,341 B1 | 11/2002 | Hunter et al. |
| 6,478,802 B2 | 11/2002 | Kienzle et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,496,188 B1 | 12/2002 | Deschamps et al. |
| 6,498,477 B1 | 12/2002 | Govari et al. |
| 6,498,944 B1 | 12/2002 | Ben-Haim et al. |
| 6,499,488 B1 | 12/2002 | Hunter et al. |
| 6,501,848 B1 | 12/2002 | Carroll et al. |
| 6,501,981 B1 | 12/2002 | Schweikard et al. |
| 6,503,195 B1 | 1/2003 | Keller et al. |
| 6,505,065 B1 | 1/2003 | Yanof et al. |
| 6,516,046 B1 | 2/2003 | Froehlich et al. |
| 6,517,534 B1 | 2/2003 | Mcgovern et al. |
| 6,522,907 B1 | 2/2003 | Bladen et al. |
| 6,526,162 B2 | 2/2003 | Asano et al. |
| 6,527,443 B1 | 3/2003 | Vilsmeier et al. |
| 6,535,756 B1 | 3/2003 | Simon et al. |
| 6,551,325 B1 | 4/2003 | Neubauer et al. |
| 6,556,696 B1 | 4/2003 | Summers et al. |
| 6,558,333 B2 | 5/2003 | Gilboa et al. |
| 6,574,492 B1 | 6/2003 | Ben-Haim et al. |
| 6,574,498 B1 | 6/2003 | Gilboa |
| 6,578,579 B2 | 6/2003 | Burnside et al. |
| 6,580,938 B1 | 6/2003 | Acker |
| 6,584,174 B2 | 6/2003 | Schubert et al. |

(56) References Cited

U.S. PATENT DOCUMENTS

| | | |
|---|---|---|
| 6,585,763 B1 | 7/2003 | Keilman et al. |
| 6,591,129 B1 | 7/2003 | Ben-Haim et al. |
| 6,593,884 B1 | 7/2003 | Gilboa et al. |
| 6,603,868 B1 | 8/2003 | Ludwig et al. |
| 6,609,022 B2 | 8/2003 | Vilsmeier et al. |
| 6,611,700 B1 | 8/2003 | Vilsmeier et al. |
| 6,611,793 B1 | 8/2003 | Burnside et al. |
| 6,615,155 B2 | 9/2003 | Gilboa |
| 6,618,612 B1 | 9/2003 | Acker et al. |
| 6,628,980 B2 | 9/2003 | Atalar et al. |
| 6,650,927 B1 | 11/2003 | Keidar |
| 6,651,669 B1 | 11/2003 | Burnside |
| 6,694,163 B1 | 2/2004 | Vining |
| 6,757,557 B1 | 6/2004 | Bladen et al. |
| 6,783,523 B2 | 8/2004 | Qin et al. |
| 6,792,390 B1 | 9/2004 | Burnside et al. |
| 6,829,379 B1 | 12/2004 | Knoplioch et al. |
| 6,833,814 B2 | 12/2004 | Gilboa et al. |
| 6,850,794 B2 | 2/2005 | Shahidi |
| 6,892,090 B2 | 5/2005 | Verard et al. |
| 6,898,263 B2 | 5/2005 | Avinash et al. |
| 6,909,913 B2 | 6/2005 | Vining |
| 6,920,347 B2 | 7/2005 | Simon et al. |
| 6,925,200 B2 | 8/2005 | Wood et al. |
| 7,006,677 B2 | 2/2006 | Manjeshwar et al. |
| 7,072,501 B2 | 7/2006 | Wood et al. |
| 7,085,400 B1 | 8/2006 | Holsing et al. |
| 7,096,148 B2 | 8/2006 | Anderson et al. |
| 7,149,564 B2 | 12/2006 | Vining et al. |
| 7,167,180 B1 | 1/2007 | Shibolet |
| 7,174,202 B2 | 2/2007 | Bladen et al. |
| 7,179,220 B2 | 2/2007 | Kukuk |
| 7,236,558 B2 | 6/2007 | Saito et al. |
| 7,301,332 B2 | 11/2007 | Govari et al. |
| 7,315,639 B2 | 1/2008 | Kuhnigk |
| 7,324,104 B1 | 1/2008 | Bitter et al. |
| 7,336,809 B2 | 2/2008 | Zeng et al. |
| 7,397,937 B2 | 7/2008 | Schneider et al. |
| 7,428,334 B2 | 9/2008 | Schoisswohl et al. |
| 7,452,357 B2 | 11/2008 | Megele et al. |
| 7,505,809 B2 | 3/2009 | Strommer et al. |
| 7,517,320 B2 | 4/2009 | Wibowo et al. |
| 7,518,619 B2 | 4/2009 | Stoval et al. |
| 7,551,759 B2 | 6/2009 | Hristov et al. |
| 7,630,752 B2 | 12/2009 | Viswanathan |
| 7,630,753 B2 | 12/2009 | Simon et al. |
| 7,659,912 B2 | 2/2010 | Akimoto et al. |
| 7,702,153 B2 | 4/2010 | Hong et al. |
| 7,751,865 B2 | 7/2010 | Jascob et al. |
| 7,756,316 B2 | 7/2010 | Odry et al. |
| 7,788,060 B2 | 8/2010 | Schneider |
| 7,792,565 B2 | 9/2010 | Vining |
| 7,805,269 B2 | 9/2010 | Glossop |
| 7,809,176 B2 | 10/2010 | Gündel |
| 7,811,294 B2 | 10/2010 | Strommer et al. |
| 7,822,461 B2 | 10/2010 | Geiger et al. |
| 7,901,348 B2 | 3/2011 | Soper et al. |
| 7,907,772 B2 | 3/2011 | Wang et al. |
| 7,916,918 B2 | 3/2011 | Suri et al. |
| 7,929,014 B2 | 4/2011 | Akimoto et al. |
| 7,951,070 B2 | 5/2011 | Ozaki et al. |
| 7,969,142 B2 | 6/2011 | Krueger et al. |
| 7,985,187 B2 | 7/2011 | Wibowo et al. |
| 8,009,891 B2 | 8/2011 | Vaan |
| 8,049,777 B2 | 11/2011 | Akimoto et al. |
| 8,055,323 B2 | 11/2011 | Sawyer |
| 8,102,416 B2 | 1/2012 | Ito et al. |
| 8,126,241 B2 | 2/2012 | Zarkh et al. |
| 8,131,344 B2 | 3/2012 | Strommer et al. |
| 8,170,328 B2 | 5/2012 | Masumoto et al. |
| 8,199,981 B2 | 6/2012 | Koptenko et al. |
| 8,200,314 B2 | 6/2012 | Bladen et al. |
| 8,202,213 B2 | 6/2012 | Ito et al. |
| 8,208,708 B2 | 6/2012 | Homan et al. |
| 8,219,179 B2 | 7/2012 | Ganatra et al. |
| 8,257,346 B2 | 9/2012 | Qin et al. |
| 8,267,927 B2 | 9/2012 | Dalal et al. |
| 8,290,228 B2 | 10/2012 | Cohen et al. |
| 8,298,135 B2 | 10/2012 | Ito et al. |
| 8,335,359 B2 | 12/2012 | Fidrich et al. |
| 8,391,952 B2 | 3/2013 | Anderson |
| 8,417,009 B2 | 4/2013 | Mizuno |
| 8,482,606 B2 | 7/2013 | Razzaque et al. |
| 8,494,612 B2 | 7/2013 | Vetter et al. |
| 8,509,877 B2 | 8/2013 | Mori et al. |
| 8,625,869 B2 | 1/2014 | Harder et al. |
| 8,672,836 B2 | 3/2014 | Higgins et al. |
| 8,682,045 B2 | 3/2014 | Vining et al. |
| 8,696,549 B2 | 4/2014 | Holsing et al. |
| 8,698,806 B2 | 4/2014 | Kunert et al. |
| 8,700,132 B2 | 4/2014 | Ganatra et al. |
| 8,706,184 B2 | 4/2014 | Mohr et al. |
| 8,706,193 B2 | 4/2014 | Govari et al. |
| 8,709,034 B2 | 4/2014 | Keast et al. |
| 8,730,237 B2 | 5/2014 | Ruijters et al. |
| 8,768,029 B2 | 7/2014 | Helm et al. |
| 8,784,400 B2 | 7/2014 | Roschak |
| 8,798,227 B2 | 8/2014 | Tsukagoshi et al. |
| 8,798,339 B2 | 8/2014 | Mielekamp et al. |
| 8,801,601 B2 | 8/2014 | Prisco et al. |
| 8,819,591 B2 | 8/2014 | Wang et al. |
| 8,827,934 B2 | 9/2014 | Chopra et al. |
| 8,828,023 B2 | 9/2014 | Neff et al. |
| 8,862,204 B2 | 10/2014 | Sobe et al. |
| 9,008,754 B2 | 4/2015 | Steinberg et al. |
| 9,129,048 B2 | 9/2015 | Stonefield et al. |
| 9,247,992 B2 | 2/2016 | Ladtkow et al. |
| 9,259,269 B2 | 2/2016 | Ladtkow et al. |
| 9,433,390 B2 | 9/2016 | Nathaniel et al. |
| 9,459,770 B2 | 10/2016 | Baker |
| 9,575,140 B2 | 2/2017 | Zur |
| 9,592,095 B2 | 3/2017 | Panescu et al. |
| 9,603,668 B2 | 3/2017 | Weingarten et al. |
| 9,770,216 B2 | 9/2017 | Brown et al. |
| 9,833,167 B2 | 12/2017 | Cohen et al. |
| 9,848,953 B2 | 12/2017 | Weingarten et al. |
| 9,888,898 B2 | 2/2018 | Imagawa et al. |
| 9,918,659 B2 | 3/2018 | Chopra et al. |
| 9,974,525 B2 | 5/2018 | Weingarten et al. |
| 10,127,629 B2 | 11/2018 | Razzaque et al. |
| 10,130,316 B2 | 11/2018 | Funabasama et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,610,306 B2 | 4/2020 | Chopra |
| 10,638,953 B2 | 5/2020 | Duindam et al. |
| 10,674,970 B2 | 6/2020 | Averbuch et al. |
| 10,682,070 B2 | 6/2020 | Duindam |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,842,575 B2 | 11/2020 | Panescu et al. |
| 10,885,630 B2 | 1/2021 | Li et al. |
| 10,896,506 B2 | 1/2021 | Zhao et al. |
| 2001/0007918 A1 | 7/2001 | Vilsmeier et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2001/0038705 A1 | 11/2001 | Rubbert et al. |
| 2002/0022837 A1 | 2/2002 | Mazzocchi et al. |
| 2002/0045916 A1 | 4/2002 | Gray et al. |
| 2002/0045919 A1 | 4/2002 | Johansson-Ruden et al. |
| 2002/0065461 A1 | 5/2002 | Cosman |
| 2002/0082498 A1 | 6/2002 | Wendt et al. |
| 2002/0095081 A1 | 7/2002 | Vilsmeier |
| 2002/0128565 A1 | 9/2002 | Rudy |

(56) References Cited

U.S. PATENT DOCUMENTS

| | | |
|---|---|---|
| 2002/0137014 A1 | 9/2002 | Anderson et al. |
| 2002/0143324 A1 | 10/2002 | Edwards et al. |
| 2002/0165448 A1 | 11/2002 | Ben-Haim et al. |
| 2002/0173689 A1 | 11/2002 | Kaplan |
| 2002/0193686 A1 | 12/2002 | Gilboa |
| 2003/0013972 A1 | 1/2003 | Makin |
| 2003/0018251 A1 | 1/2003 | Solomon |
| 2003/0074011 A1 | 4/2003 | Gilboa et al. |
| 2003/0086599 A1 | 5/2003 | Armato et al. |
| 2003/0095692 A1 | 5/2003 | Mundy et al. |
| 2003/0099390 A1 | 5/2003 | Zeng et al. |
| 2003/0142753 A1 | 7/2003 | Gunday |
| 2003/0144658 A1 | 7/2003 | Schwartz et al. |
| 2003/0160721 A1 | 8/2003 | Gilboa et al. |
| 2003/0164952 A1 | 9/2003 | Deichmann et al. |
| 2003/0197686 A1 | 10/2003 | Usuda |
| 2003/0216639 A1 | 11/2003 | Gilboa et al. |
| 2004/0000249 A1 | 1/2004 | Avetisian |
| 2004/0006268 A1 | 1/2004 | Gilboa et al. |
| 2004/0015049 A1 | 1/2004 | Zaar |
| 2004/0019350 A1 | 1/2004 | O'brien et al. |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0122310 A1 | 6/2004 | Lim |
| 2004/0138548 A1 | 7/2004 | Strommer et al. |
| 2004/0143317 A1 | 7/2004 | Stinson et al. |
| 2004/0169509 A1 | 9/2004 | Czipott et al. |
| 2004/0215181 A1 | 10/2004 | Christopherson et al. |
| 2004/0249267 A1 | 12/2004 | Gilboa |
| 2004/0254454 A1 | 12/2004 | Kockro |
| 2005/0018885 A1 | 1/2005 | Chen et al. |
| 2005/0027193 A1 | 2/2005 | Mitschke et al. |
| 2005/0033149 A1 | 2/2005 | Strommer et al. |
| 2005/0059890 A1 | 3/2005 | Deal et al. |
| 2005/0085715 A1 | 4/2005 | Dukesherer et al. |
| 2005/0090818 A1 | 4/2005 | Pike, Jr. et al. |
| 2005/0107688 A1 | 5/2005 | Strommer |
| 2005/0119527 A1 | 6/2005 | Banik et al. |
| 2005/0154282 A1 | 7/2005 | Li et al. |
| 2005/0182295 A1 | 8/2005 | Soper et al. |
| 2005/0197566 A1 | 9/2005 | Strommer et al. |
| 2005/0207630 A1 | 9/2005 | Chan et al. |
| 2005/0272971 A1 | 12/2005 | Ohnishi et al. |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0079759 A1 | 4/2006 | Vaillant et al. |
| 2006/0116575 A1 | 6/2006 | Willis |
| 2006/0149134 A1 | 7/2006 | Soper et al. |
| 2006/0241396 A1 | 10/2006 | Fabian et al. |
| 2006/0241399 A1 | 10/2006 | Fabian |
| 2006/0253030 A1 | 11/2006 | Altmann et al. |
| 2007/0078334 A1 | 4/2007 | Scully et al. |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167801 A1 | 7/2007 | Webler et al. |
| 2007/0167804 A1 | 7/2007 | Park et al. |
| 2007/0167806 A1 | 7/2007 | Wood et al. |
| 2007/0225553 A1 | 9/2007 | Shahidi |
| 2007/0232882 A1 | 10/2007 | Glossop et al. |
| 2007/0232898 A1 | 10/2007 | Huynh et al. |
| 2007/0265639 A1 | 11/2007 | Danek et al. |
| 2007/0287901 A1 | 12/2007 | Strommer et al. |
| 2008/0008367 A1 | 1/2008 | Franaszek et al. |
| 2008/0008368 A1 | 1/2008 | Matsumoto |
| 2008/0018468 A1 | 1/2008 | Volpi et al. |
| 2008/0033452 A1 | 2/2008 | Vetter et al. |
| 2008/0086051 A1 | 4/2008 | Voegele |
| 2008/0097154 A1 | 4/2008 | Makower et al. |
| 2008/0097187 A1 | 4/2008 | Gielen et al. |
| 2008/0118135 A1 | 5/2008 | Averbuch et al. |
| 2008/0123921 A1 | 5/2008 | Gielen et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0183073 A1 | 7/2008 | Higgins et al. |
| 2008/0188749 A1 | 8/2008 | Rasche et al. |
| 2008/0212881 A1 | 9/2008 | Hirakawa |
| 2008/0243142 A1 | 10/2008 | Gildenberg |
| 2008/0247622 A1 | 10/2008 | Aylward et al. |
| 2009/0012390 A1 | 1/2009 | Pescatore et al. |
| 2009/0030306 A1 | 1/2009 | Miyoshi et al. |
| 2009/0082665 A1 | 3/2009 | Anderson |
| 2009/0096807 A1 | 4/2009 | Silverstein et al. |
| 2009/0182224 A1 | 7/2009 | Shmarak et al. |
| 2009/0189820 A1 | 7/2009 | Saito et al. |
| 2009/0284255 A1 | 11/2009 | Zur |
| 2009/0318797 A1 | 12/2009 | Hadani |
| 2010/0016658 A1 | 1/2010 | Zou et al. |
| 2010/0290693 A1 | 11/2010 | Cohen et al. |
| 2010/0310146 A1 | 12/2010 | Higgins et al. |
| 2010/0312094 A1 | 12/2010 | Guttman et al. |
| 2011/0085720 A1 | 4/2011 | Averbuch |
| 2011/0236868 A1 | 9/2011 | Bronstein et al. |
| 2011/0237897 A1 | 9/2011 | Gilboa |
| 2011/0251607 A1 | 10/2011 | Kruecker et al. |
| 2012/0120091 A1 | 5/2012 | Koudijs et al. |
| 2012/0184844 A1 | 7/2012 | Gielen et al. |
| 2012/0188352 A1 | 7/2012 | Wittenberg et al. |
| 2012/0190923 A1 | 7/2012 | Kunz et al. |
| 2012/0203065 A1 | 8/2012 | Higgins et al. |
| 2012/0249546 A1 | 10/2012 | Tschirren et al. |
| 2012/0280135 A1 | 11/2012 | Bal |
| 2012/0287238 A1 | 11/2012 | Onishi et al. |
| 2013/0063434 A1 | 3/2013 | Miga et al. |
| 2013/0165854 A1 | 6/2013 | Sandhu et al. |
| 2013/0231556 A1 | 9/2013 | Holsing et al. |
| 2013/0303945 A1 | 11/2013 | Blumenkranz et al. |
| 2013/0317352 A1 | 11/2013 | Case et al. |
| 2014/0035798 A1 | 2/2014 | Kawada et al. |
| 2014/0066766 A1 | 3/2014 | Stonefield et al. |
| 2014/0336461 A1 | 11/2014 | Reiter et al. |
| 2015/0148690 A1 | 5/2015 | Chopra et al. |
| 2015/0265257 A1 | 9/2015 | Costello et al. |
| 2015/0265368 A1 | 9/2015 | Chopra et al. |
| 2015/0305612 A1 | 10/2015 | Hunter et al. |
| 2016/0000302 A1 | 1/2016 | Brown et al. |
| 2016/0000356 A1 | 1/2016 | Brown et al. |
| 2016/0005193 A1 | 1/2016 | Markov et al. |
| 2016/0005220 A1 | 1/2016 | Weingarten et al. |
| 2016/0038248 A1 | 2/2016 | Bharadwaj et al. |
| 2016/0073854 A1 | 3/2016 | Zeien |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0035379 A1* | 2/2017 | Weingarten ............ A61B 6/547 |
| 2017/0112576 A1 | 4/2017 | Coste-Maniere et al. |
| 2017/0135760 A1 | 5/2017 | Girotto et al. |
| 2017/0156685 A1* | 6/2017 | Dickhans ............... A61B 6/032 |
| 2017/0172664 A1 | 6/2017 | Weingarten et al. |
| 2017/0209071 A1 | 7/2017 | Zhao et al. |
| 2017/0258526 A1 | 9/2017 | Lang |
| 2017/0265952 A1 | 9/2017 | Donhowe et al. |
| 2017/0280970 A1 | 10/2017 | Sartor et al. |
| 2017/0311844 A1 | 11/2017 | Zhao et al. |
| 2017/0319165 A1 | 11/2017 | Averbuch |
| 2017/0345155 A1 | 11/2017 | Higgins et al. |
| 2017/0361093 A1 | 12/2017 | Yoo et al. |
| 2018/0078318 A1 | 3/2018 | Barbagli et al. |
| 2018/0085079 A1 | 3/2018 | Krimsky |
| 2018/0146839 A1 | 5/2018 | Friedlander et al. |
| 2018/0153621 A1 | 6/2018 | Duindam et al. |

(56) References Cited

U.S. PATENT DOCUMENTS

| | | |
|---|---|---|
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0027252 A1 | 1/2019 | Calhoun et al. |
| 2019/0038359 A1 | 2/2019 | Weingarten et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0139216 A1 | 5/2019 | Georgescu et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0015925 A1 | 1/2020 | Scheib |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0155116 A1 | 5/2020 | Donhowe et al. |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188038 A1 | 6/2020 | Donhowe et al. |
| 2020/0188047 A1 | 6/2020 | Itkowitz et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |

FOREIGN PATENT DOCUMENTS

| | | |
|---|---|---|
| CA | 964149 A | 3/1975 |
| CN | 103068294 A | 4/2013 |
| CZ | 486540 | 9/2016 |
| CZ | 2709512 | 8/2017 |
| CZ | 2884879 | 1/2020 |
| DE | 3042343 A1 | 6/1982 |
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T | 11/2002 |
| DE | 102009043523 A1 | 4/2011 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0651968 A1 | 5/1995 |
| EP | 0655138 A1 | 5/1995 |
| EP | 0796633 A1 | 9/1997 |
| EP | 0829229 A1 | 3/1998 |
| EP | 0857461 A2 | 8/1998 |
| EP | 0894473 A2 | 2/1999 |
| EP | 0908146 A2 | 4/1999 |
| EP | 0922966 A2 | 6/1999 |
| EP | 0930046 A2 | 7/1999 |
| EP | 1078644 A1 | 2/2001 |
| EP | 2096523 A1 | 9/2009 |
| EP | 2117436 A2 | 11/2009 |
| EP | 1499235 B1 | 8/2016 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| FR | 2417970 A1 | 9/1979 |
| FR | 2618211 A1 | 1/1989 |
| GB | 2094590 A | 9/1982 |
| GB | 2164856 A | 4/1986 |
| GB | 2197078 A | 5/1988 |
| JP | S63240851 A | 10/1988 |
| JP | H03267054 A | 11/1991 |
| JP | H06194639 A | 7/1994 |
| JP | H07159378 A | 6/1995 |
| JP | H08233601 A | 9/1996 |
| JP | H08299305 A | 11/1996 |
| JP | H0325752 B | 11/1997 |
| JP | 2002306403 A | 10/2002 |
| JP | 2003290131 A | 10/2003 |
| JP | 2005287900 A | 10/2005 |
| JP | 2006204635 A | 8/2006 |
| JP | 2009018184 A | 1/2009 |
| JP | 2009078133 A | 4/2009 |
| JP | 2010279695 A | 12/2010 |
| JP | 2011193885 A | 10/2011 |
| JP | 2013506861 A | 2/2013 |
| MX | PA03005028 A | 1/2004 |
| MX | 225663 B | 1/2005 |
| MX | 226292 | 2/2005 |

(56) References Cited

FOREIGN PATENT DOCUMENTS

| | | |
|---|---|---|
| MX | 246862 B | 6/2007 |
| MX | 265247 | 3/2009 |
| MX | 284569 B | 3/2011 |
| WO | 2000010456 A1 | 3/2000 |
| WO | 2001067035 A1 | 9/2001 |
| WO | 03086498 A2 | 10/2003 |
| WO | 03086498 A3 | 10/2003 |
| WO | 2009138871 A2 | 11/2009 |
| WO | 2011102012 A1 | 8/2011 |
| WO | 2013192598 A1 | 12/2013 |
| WO | 2015149040 A1 | 10/2015 |

OTHER PUBLICATIONS

Communication pursuant to Article 94(3) EPC issued in European Patent Application No. 20188309.7 dated Oct. 17, 2023.

* cited by examiner

CONE BEAM AND 3D FLUOROSCOPE LUNG NAVIGATION

FIELD

The disclosure relates to methods and systems for reducing divergence between computed tomography images and a patient through the use of cone beam computed tomography imaging.

BACKGROUND

Pulmonary disease may cause one or more portions of a patient's lungs may lose its ability to function normally and thus may need to be treated. Lung treatment procedures may be very complex and would be greatly aided if the surgeon performing the procedure can visualize the way airways and other structures in the patient's lungs are shaped and where tools are located. Traditional pre-operative images are helpful, to an extent, with the former, but provide no guidance with regard to the latter.

Systems for displaying images and tracking tools in the patient's lungs generally rely on pre-operative data, such as from computed tomography (CT) scans performed before, sometimes days or weeks in advance, the treatment procedure begins. However, such systems do not account for changes that may have occurred after the CT scan was performed, or for movement occurring during the treatment procedure. Systems, devices, and methods for improving on the process of identifying and visualizing a patient's lungs, as well as structures and tools located therein, are described below.

SUMMARY

The disclosure is directed to a systems and method of a method of registering an image to a luminal network including detecting a position of a sensor in a luminal network. The method of registering also includes receiving images for 3D reconstruction of the luminal network with the sensor within the luminal network; presenting the 3D reconstruction image on a user interface; receiving indication of location of target in the 3D reconstruction image; generating pathway through the luminal network to a target; and determining if the sensor moved from detected position following receipt of the images for 3D reconstruction, where when it is determined that the position of the sensor is the same as detected position, the luminal network and the 3D reconstruction are registered. Other embodiments of this aspect include corresponding computer systems, apparatus, and computer programs recorded on one or more computer storage devices, each configured to perform the actions of the methods.

Implementations may include one or more of receiving survey data when it is determined that the position of the sensor has changed, registering the luminal network to the 3D reconstruction based on the survey data or generating a 3D model of the luminal network. The method may further include displaying the pathway on in the 3D reconstruction, 2D slices images derived from the 3D reconstruction, a 3D model derived from the 3D reconstruction, or a virtual bronchoscopy. Additionally, or alternatively, the method may further include displaying the position of the sensor along the pathway in a user interface.

Another aspect of the disclosure is a method of registering an image to a luminal network including receiving a pre-operative computed tomography (CT) image of the luminal network, receiving an indication of a target within the luminal network, generating a pathway through the luminal network to the target. The method of registering also includes receiving images for 3D reconstruction of the luminal network, transforming coordinates of the pre-operative CT image to coordinates of the 3D reconstruction to register the pre-operative CT image to the 3D reconstruction, and updating a position of a catheter in the 3D reconstruction image or a 3D model upon detection of movement of the catheter.

The method may further include displaying the 3D reconstruction, 2D slices images derived from the 3D reconstruction, a 3D model derived from the 3D reconstruction, or a virtual bronchoscopy on a user interface. In another aspect the method includes generating a 3D model from the 3D reconstruction image before transforming the pre-operative CT coordinates and the 3D reconstruction coordinates and may also include matching features from the CT images to the 3D reconstruction and 3D model derived from the 3D reconstruction. Alternatively, the method includes generating a 3D model from the 3D reconstruction after transferring the target and pathway from the pre-operative CT image to the 3D reconstruction. The method may include receiving survey data, where the survey data is received prior to receipt of the 3D reconstruction or the survey data is received after transfer of the target and pathway to the 3D reconstruction from the pre-operative CT image to register the 3D reconstruction to the luminal network.

A further aspect of the disclosure is a method for registering an image to a luminal network including receiving a pre-operative computed tomography (CT) image of the luminal network, receiving an indication of a target within the luminal network, generating a pathway through the luminal network to the target, generating a CT 3D model, detecting a position of a catheter within the luminal network, registering the pre-operative CT image to the detected position of the catheter, receiving an indication of a location of a sensor in the pre-operative CT or CT 3D model and update the location in a user interface until proximate the target, receiving images for 3D reconstruction of the luminal network, and detecting a position of the catheter and updating the position on a use interface.

The method may further include generating a 3D model from the 3D reconstruction. Still further the method may include recalling survey data from memory, presenting the 3D reconstruction on a user interface, receive an indication of a location of a target in the 3D reconstruction, and generating a pathway in the 3D reconstruction or 3D model. Still further the method may further include determining a relative position of the target and the catheter in the 3D reconstruction and updating the relative position of the target and the catheter in the pre-operative CT image and CT 3D model based on the determined relative position in the 3D reconstruction or 3D model. Additionally, the method may include registering the pre-operative CT image with the 3D reconstruction and transferring the target and pathway from the pre-operative CT image and 3D model to the 3D reconstruction and 3D model.

BRIEF DESCRIPTION OF THE DRAWINGS

Various aspects and features of the disclosure are described hereinbelow with references to the drawings, wherein.

DETAILED DESCRIPTION

The disclosure is directed to a system and method for using a cone beam computed tomography (CBCT) image or a 3D fluoroscopy image in connection with intraluminal navigation techniques and systems.

There exist a number of systems that utilize the output from a pre-procedural computed tomography (CT) scan (e.g., CT image data) for purposes of identifying areas of interest or targets to which navigation of an endoscope or catheter is desired. Typically, this navigation will be of luminal networks such as the airways of the lungs or the biliary tract, but they could also be of spaces such as the thoracic cavity generally or other locations within a patient. These systems generally have two phases. A first phase is a planning phase where the targets are identified, and a three-dimensional (3D) model is generated. A second phase is a navigation phase where the location of the catheter within the patient is detected and depicted on the 3D model or other images to allow the clinician to navigate to the identified targets. By updating the position of a catheter within the 3D model, the clinician is able to perform procedures such as biopsy or treatment at the target location. One such systems is the ILLUMISITE system sold by Medtronic PLC, which is an electromagnetic navigation (EMN) system.

Figure 1:
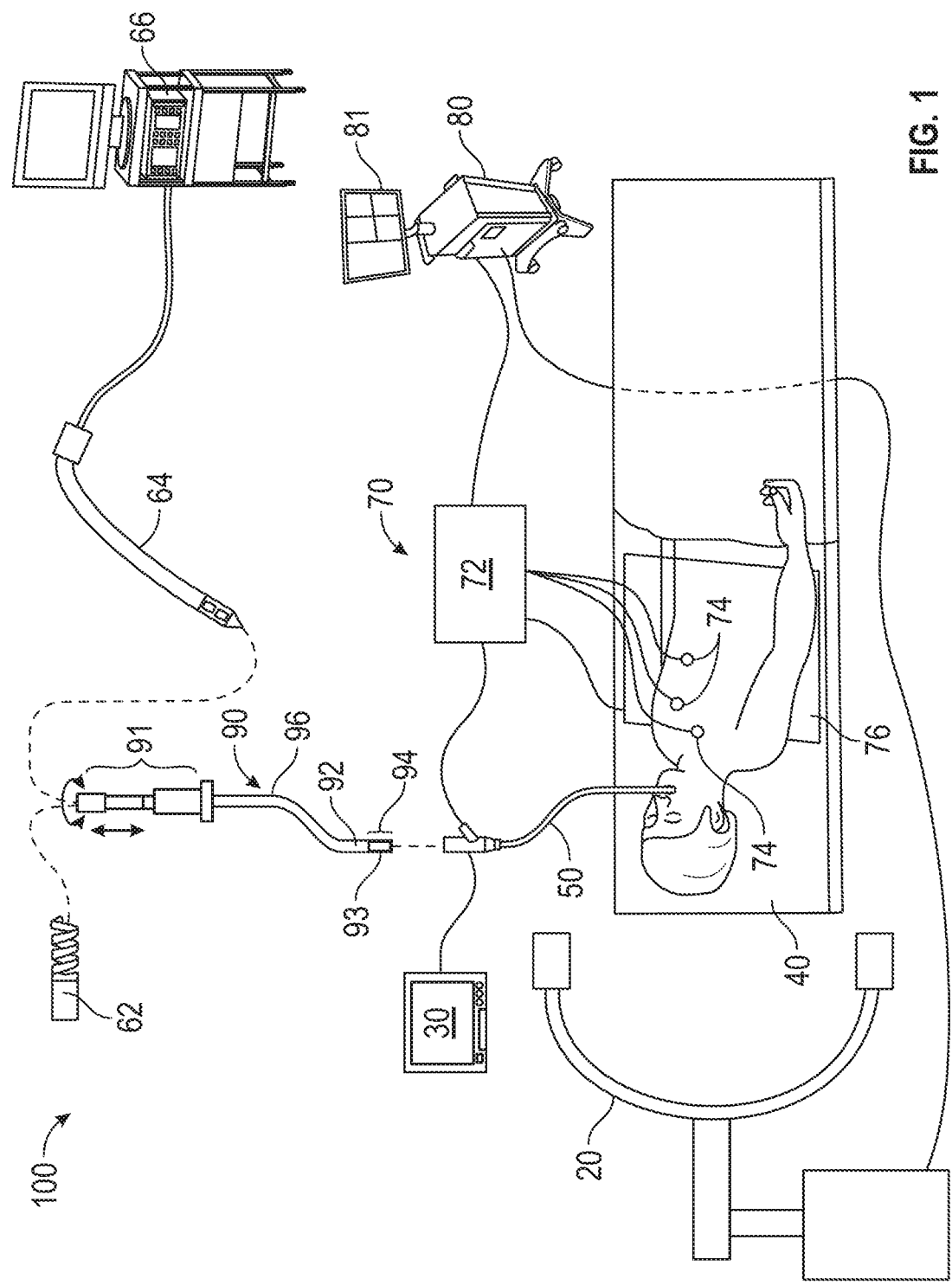
FIG. 1 is a schematic diagram depicting an imaging and navigation system in accordance with the disclosure.

FIG. 1 depicts a system 100 suitable for implementing methods described herein. As shown in FIG. 1, system 100 is used to perform one or more procedures on a patient supported on an operating table 40. In this regard, system 100 generally includes a bronchoscope 50, monitoring equipment 30, a tracking system 70, and a computing device 80.

Bronchoscope 50 is configured for insertion through the patient's mouth and/or nose into the patient's airways. Bronchoscope 50 includes a source of illumination and a video imaging system (not explicitly shown) and is coupled to monitoring equipment 30, for example, a video display, for displaying the video images received from the video imaging system of bronchoscope 50. In an embodiment, bronchoscope 50 may operate in conjunction with a catheter guide assembly 90. Catheter guide assembly 90 includes a locatable guide (LG) 92 and catheter 96. Catheter 96 may act as an extended working channel (EWC) and be configured for insertion through a working channel of bronchoscope 50 into the patient's airways (although the catheter guide assembly 90 may alternatively be used without bronchoscope 50). Catheter guide assembly 90 includes a handle 91 connected to catheter 96, and which can be manipulated by rotation and compression to steer LG 92 and catheter 96, catheter 96 is sized for placement into the working channel of bronchoscope 50. In the operation of catheter guide assembly 90, LG 92, including an EM sensor 94, is inserted into catheter 96 and locked into position such that EM sensor 94 extends a desired distance beyond a distal tip 93 of catheter 96. The location of EM sensor 94, and thus distal tip 93 of catheter 96, within an EM field generated by EM field generator 76, can be derived by tracking module 72 and computing device 80.

LG 92 and catheter 96 are selectively lockable relative to one another via a locking mechanism 99. A six degrees-of-freedom tracking system 70 is utilized for performing navigation, although other configurations are also contemplated. Tracking system 70 may be configured for use with catheter guide assembly 90 to track a position of EM sensor 94 as it moves in conjunction with catheter 96 through the airways of the patient, as detailed below. In an embodiment, tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The six degrees of freedom coordinates of reference sensors 74 are sent as data to computing device 80, which includes an application 81, where the data from reference sensors 74 are used to calculate a patient coordinate frame of reference.

Although EM sensor 94 is described above as being included in LG 92, it is also envisioned that EM sensor 94 may be embedded or incorporated within a treatment tool, such as a biopsy tool 62 or an treatment tool 64 (e.g. an ablation catheter), where the treatment tool may alternatively be utilized for navigation without need of LG 92 or the necessary tool exchanges that use of LG 92 requires. EM sensor 94 may also be embedded or incorporated within catheter 96, such as at a distal portion of catheter 96, thereby enabling tracking of the distal portion of catheter 96 without the need for LG 92.

According to an embodiment, biopsy and treatment tools 62, 64 are configured to be insertable into catheter guide assembly 90 following navigation to a target location and removal of LG 92. Biopsy tool 62 may be used to collect one or more tissue samples from the target location, and in an embodiment, is further configured for use in conjunction with tracking system 70 to facilitate navigation of biopsy tool 62 to the target location, and tracking of a location of biopsy tool 62 as it is manipulated relative to the target location to obtain the tissue sample. Treatment tool 64 is configured to be operated with a generator 66, such as a radio frequency generator or a microwave generator and may include any of a variety of ablation tools and/or catheters. Though shown as a biopsy tool and microwave ablation tool in FIG. 1, those of skill in the art will recognize that other tools including for example RF ablation tools, brachytherapy tools, and others may be similarly deployed and tracked without departing from the scope of the present disclosure. Additionally, a piercing tool and/or puncture tool may be used with and/or incorporated in LG 92 to create an exit point where LG 92, and thereby catheter 96, is navigated outside of the patient's airways and toward the target location, as further described below.

A radiographic imaging device 20, such as a C-arm imaging device capable of capturing images of at least a portion of the patient's lungs is used in conjunction with system 100. Radiographic imaging device 20 captures images from which a 3D reconstruction can be generated such as a CBCT device or a 3D fluoroscopy device. Generally, both CBCT images and 3D fluoroscopy images are captured by sweeping the radiographic imaging device 20 through a defined sweep angle (e.g., 30-180 degrees and any integer value within that range). By processing the individual images or video captured during the sweep, a 3D reconstruction can be generated which is similar to a traditional CT image. As will be understood CBCT images have similar resolution to CT images whereas fluoroscopy images have a lower resolution.

Figure 1A:
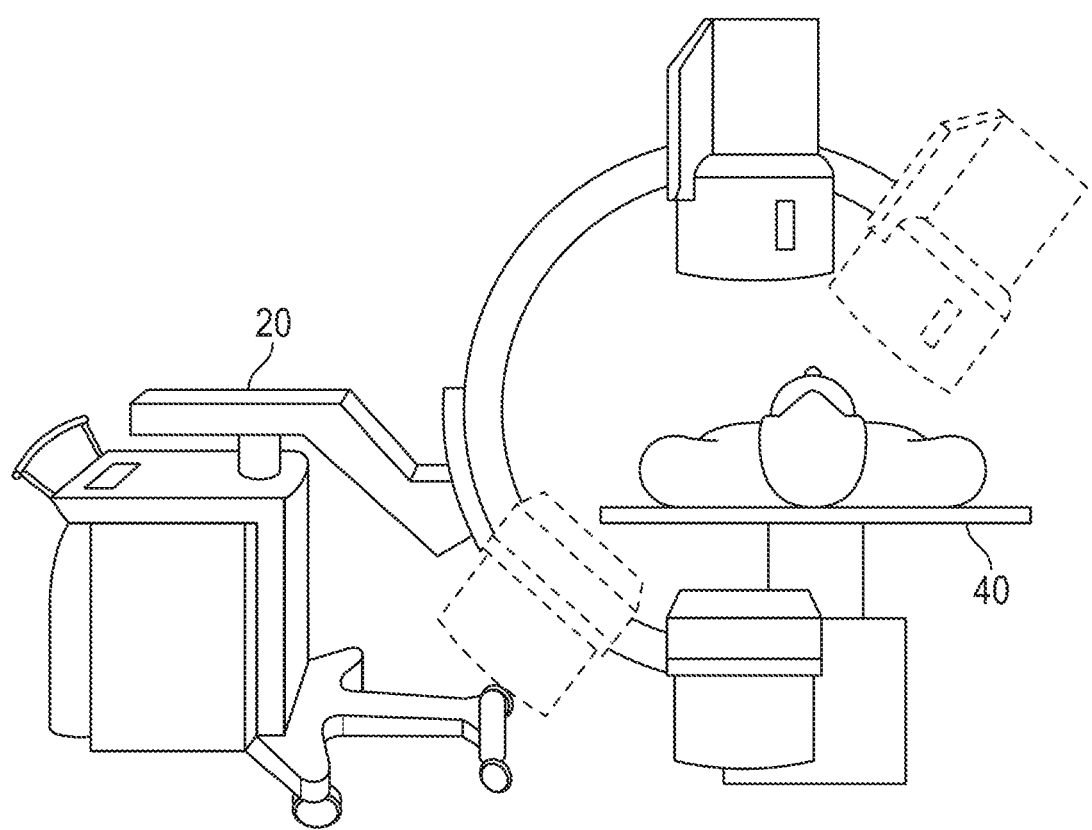
FIG. 1A is a schematic diagram depicting an end view of the imaging and navigation system of FIG. 1 in accordance with aspects of het disclosure.

As shown in FIG. 1, radiographic imaging device 20 is connected to computing device 80 such that application 81 may receive and process image data obtained by radiographic imaging device 20. However, radiographic imaging device 20 may also have a separate computing device located within itself, within the treatment room or in a separate control room to first receive the image data obtained by radiographic imaging device 20 and relay such image data to computing device 80. In one example, the radiographic imaging device 20 is connected to a picture archiving and communications system (PACS) server which in turn is connected to the computing device 80 and application 81. To avoid exposing the clinician to unnecessary radiation from repeated radiographic scans, the clinician may exit the treatment room and wait in an adjacent room, such as the control room, while radiographic imaging device 20 performs the CBCT and/or fluoroscopic scans. FIG. 1A depicts an end view of the radiographic imaging device as it might be used to image a patient while they are laying on table 40 in accordance with the disclosure.

Computing device 80 includes software and/or hardware, such as application 81, used to facilitate the various phases of an EMN procedure, including generating the 3D model, identifying a target location, planning a pathway to the target location, registering the 3D model with the patient's actual airways, navigating to the target location, and performing treatment at the target location. For example, computing device 80 utilizes data acquired from a CT scan, CBCT scan, magnetic resonance imaging (MRI) scan, positron emission tomography (PET) scan, and/or any other suitable imaging modality to generate and display the 3D model of the patient's airways, to enable identification of a target location on the 3D model (automatically, semi-automatically or manually) by analyzing the image data and/or 3D model, and allow for the determination and selection of a pathway through the patient's airways to the target location. While the image data may have gaps, omissions, and/or other imperfections included in the image data, the 3D model is a smooth representation of the patient's airways, with any such gaps, omissions, and/or imperfections in the image data filled in or corrected. The 3D model may be presented on a display monitor associated with computing device 80, or in any other suitable fashion.

Though described herein generally as generating a 3D model from either pre-operative CT images, CBCT images, or 3D fluoroscopy images, application 81 may not need to generate the 3D model or even a 3D reconstruction. Instead, that functionality may reside in the computing device associated with the radio graphic imaging device 20 or the PACS server. In such scenarios, the application 81 need merely import the 3D reconstruction or 3D model generated from a CT image, CBCT image, fluoroscopy images by the radiographic imaging device 20 or the PACS server.

Using computing device 80, various views of the image data and/or 3D model may be displayed to and manipulated by a clinician to facilitate identification of the target location. As noted above, the target location may be a site within the patient's lungs where treatment is to be performed. For example, the treatment target may be located in lung tissue adjacent to an airway. The 3D model may include, among other things, a model airway tree corresponding to the actual airways of the patient's lungs, and show the various passages, branches, and bifurcations of the patient's actual airway tree. Additionally, the 3D model may include lesions, markers, blood vessels and vascular structures, lymphatic vessels and structures, organs, other physiological structures, and/or a 3D rendering of the pleural surfaces and fissures of the patient's lungs. Some or all of the aforementioned elements may be selectively displayed, such that the clinician may choose which elements should be displayed when viewing the 3D model.

After identifying the target location, application 81 may determine a pathway between the patient's trachea and the target location via the patient's airways. In instances where the target location is located in lung tissue that is not directly adjacent an airway, at least a portion of the pathway will be located outside of the patient's airways to connect an exit point on an airway wall to the target location. In such instances, LG 92 and catheter 96 will first be navigated along a first portion of the pathway through the patient's airways to the exit point on the airway wall. LG 94 may then be removed from catheter 96 and an access tool, such as a piercing or puncture tool, inserted into catheter 96 to create an opening in the airway wall at the exit point, catheter 96 may then be advanced through the airway wall into the parenchyma surrounding the airways. The access tool may then be removed from catheter 96 and LG 92 and/or tools 62, 64 reinserted into catheter 96 to navigate catheter 96 along a second portion of the pathway outside of the airways to the target location.

During a procedure, EM sensor 94, in conjunction with tracking system 70, enables tracking of EM sensor 94 (and thus distal tip 93 of catheter 96 or tools 62, 64) as EM sensor 94 is advanced through the patient's airways following the pathway planned during the planning phase. Though generally described herein in connection with EM sensors 94, the disclosure is not so limited. Rather, the position of the bronchoscope 50, catheter 96 or tools 62, 64 can be determined through the use of flex sensors (E.g., Fiber-Bragg sensors) which are used to match the shape of the catheter 96 with the shape of the airways in the 3D model. By sensing the shape of the sensors, and matching the sensor's shape the airways, an accurate determination of the position of the sensor or a distal portion of the bronchoscope 50, catheter 96 or tools 62, 64 can be determined and displayed on the 3D model.

As an initial step of the procedure, when using a 3D model generated from CT scan, the 3D model must be registered with the patient's actual airways to enable application 81 to display an indication of the location of EM sensor 94 on the 3D model corresponding to the location of EM sensor 94 within the patient's airways. The registration is necessary because the CT scan may have been taken days, and even weeks or months prior to the actual procedure. Even if the CT scan were taken the same day, such CT scans are not undertaken within a surgical suite thus registration is still necessary.

One potential method of registration involves performing a survey of the patient's lungs by navigating LG 92 into each lobe of the patient's lungs to at least the second bifurcation of the airways of that lobe. The position of LG 92 is tracked during this registration phase, and the 3D model is iteratively updated based on the tracked position of the sensor 94 within the actual airways of the patient's lungs. While the registration process focuses on aligning the patient's actual airways with the airways of the 3D model, registration also ensures that the position of vascular structures, pleural surfaces, and fissures of the lungs are accurately determined.

Registration, however, does not achieve a perfect match of the position of the patient's lungs and the 3D model. There are a number of reasons for this mismatch, typically called CT-to-body divergence. As an initial matter, traditional CT images are taken at full breath hold. That is, the patient is asked to expand their lungs to a maximum and hold that position while undergoing the imaging. This has the benefit of inflating the airways and increasing their visibility in the CT images and make it easier to generate a highly detailed 3D model. However, when performing the procedure, the patient is not at a full breath hold, rather they are typically sedated and experiencing tidal volume breathing. This results in a difference in shape and position of the airways in the lungs of the patient during the procedure as compared to during the CT imaging. As a result, even when the airways have been registered to the 3D model (e.g., using the airway sweep or another method) there will be differences between the relative positions of the airways or targets identified in the lungs in the model and the actual relative positions of the patient's airways and the target.

One method of addressing the CT-to-body divergence is to utilize a CBCT image data set from radiographic imaging device 20 and not a traditional CT scans as the starting point for the procedure. In this process, the CBCT image data is used to generate and display the 3D model of the patient's airways, to enable identification of a target location on the 3D model (automatically, semi-automatically or manually) by analyzing the image data and/or 3D model, and allow for the determination and selection of a pathway through the patient's airways to the target location. Though the following techniques are described in connection with CBCT images those of skill in the art will appreciate that they are equally applicable to any imaging technique capable of generating a 3D reconstruction such as 3D fluoroscopy, as noted above.

Figure 2:
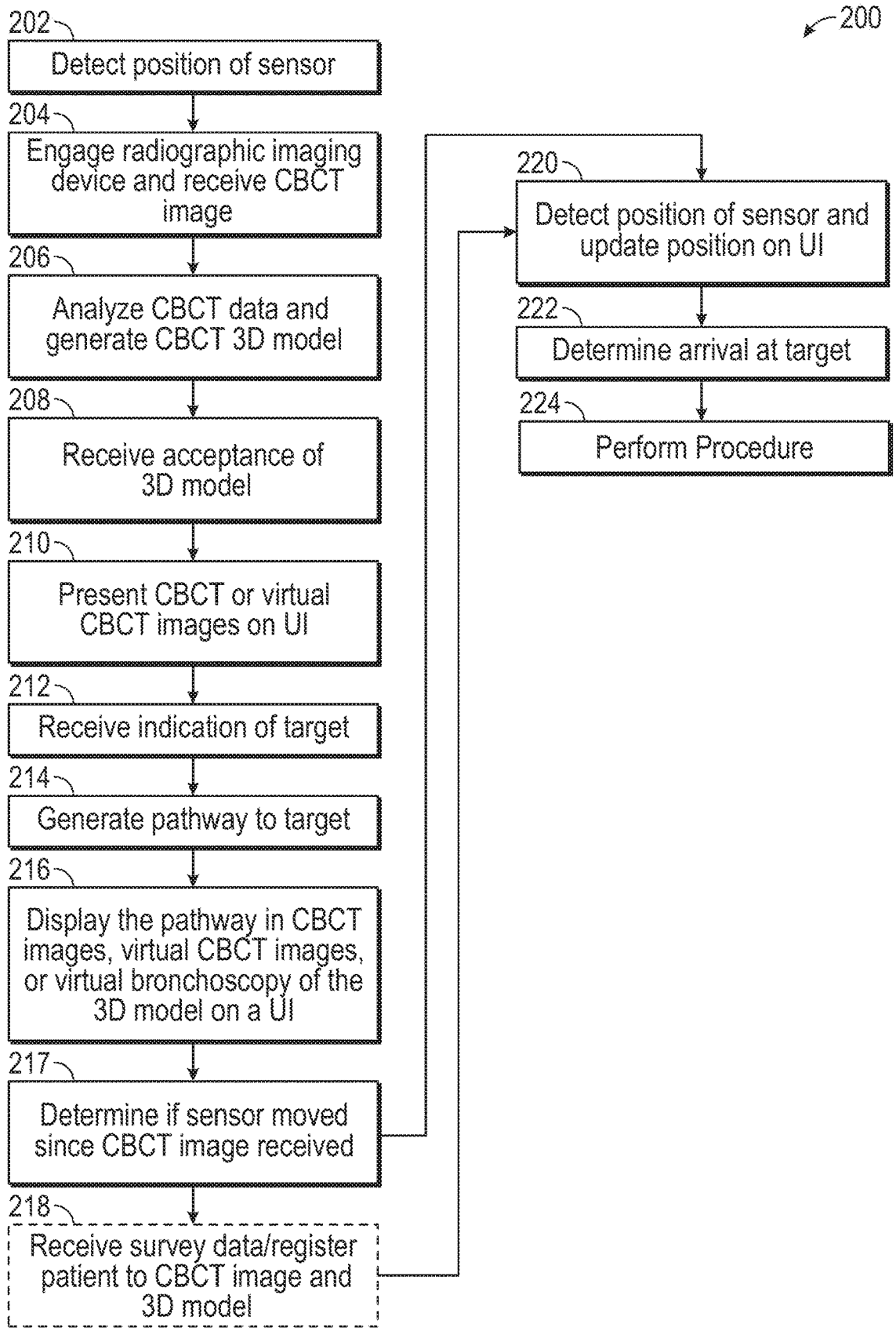
FIG. 2 is a flow chart of an imaging and navigation procedure in accordance with aspects of the disclosure.

FIG. 2 presents a method 200 for employing CBCT in conjunction with system 100 of FIG. 1 such that the planning phase occurs in conjunction with the navigation and treatment of the patient. As will be appreciated, the patient is situated on the table 40, reference sensors 74 are on the patient's chest, and connected to EM tracking system 70. A bronchoscope 50 and/or catheter 96 is inserted into the patient's airways and images may be displayed on the monitoring equipment 30. A position of the sensor 94 (e.g., one associated with the bronchoscope 50 or catheter 96 or another tool) can be detected and indication that a sensor position has been received by tracking system 70 can be presented on a user interface on computing device 80 at step 202.

Radiographic imaging device 20 may then be engaged and the computing device 80 receives the CBCT at step 204. The computing device 80 includes one or more applications for processing the CBCT data and presenting it on one or more user interfaces for manipulation and assessment. At step 206, the application analyzes the CBCT data and generates a 3D model of the airways. This 3D model can be manipulated by the user via a user-interface to ensure that it has sufficient resolution and sufficiently captures the airways of the patient (e.g., to a particular bifurcation point). A rejection of the 3D model may be received by the application at which point a further CBCT image may be acquired and the process restarted at step 204. The rejection may be based for example, on the clinician not being satisfied with the 3D model (e.g., insufficient bifurcation generation, missing a lobe or a significant portion thereof), alternatively, the 3D model may simply appear incorrect based on the clinician's experience with the physiology of patients. These types of deficiencies may be the result of improper or insufficient CBCT imaging or an improper setting on the radio graphic imaging device 120.

Acceptance of the 3D model is received by the application at step 208 and the user-interface presents CBCT images or virtual CBCT images of the patient's lungs from the CBCT at step 210. These CBCT images are slice images either taken at or generated for different points of the patient's lungs in cross section. The user interface allows the user to scroll through these images which show one or more of the axial, coronal or sagittal planes (though others are also possible) of the lungs and allows the user to identify a target within the images. The application receives the indication of a target at step 212 and generates a pathway to reach the target through airways at step 214. The target indication may be a manual marking by a clinician providing the indication through a user interface on computing device 80. Alternatively, the application 81 may perform an image analysis and automatically detect the target and provide the indication of its location. The user interface then displays the pathway though the airways in one or more CBCT images, virtual CBCT images, or a virtual bronchoscopy view of the 3D model at step 216. The user interface may additionally or alternatively display the pathway on one or more of CBCT images or virtual CBCT images.

The CBCT images will also show the presence of the bronchoscope 50 or catheter 96 that had been previously inserted into the patient. At step 217 the application can determine whether the sensor 94 has moved since the acquisition of the CBCT images. If the sensor 94 has not moved since the taking of the CBCT images in step 204, then the position of the EM sensor detected in step 202 corresponds to the position of the distal end of the bronchoscope 50 or catheter 96 in the images. As such the EM coordinate system and the CBCT image system are registered to one another and no further steps need be taken to register the patient's lungs to the 3D model generated from the CBCT images and further navigation can be undertaken following the planned pathway through the 3D model with confidence.

If the determination at step 217 is that the sensor 94 has moved, or moved greater than some threshold, then an indicator can be presented on the user interface suggesting that the user perform a survey, as described above, and the application 81 receives the survey data at step 218. The survey involves the insertion of the EM sensor 94 into the lobes of the lungs receipt by the tracking system 70 of the position of the EM sensor as it moves through the airways. As many hundreds or thousands of these positions (EMN coordinates) are collected a point cloud of positions is created. The point cloud, of which all points are assumed to be taken from within the luminal network has a 3D dimensional shape that can then be matched to the 3D shape of the airways to register to the 3D model and the airways of the patient. Once registered the detected position of the EM sensor can be used to follow a pathway in the 3D model to the identified target. The detected position of the EM sensor relative to the pathway and the target is continually updated on the user interface at step 220 until determining that the target has been is arrived at step 222 and a procedure is undertaken at step 224. The procedure may be a biopsy or a treatment of the target such as ablation (e.g., RF, microwave, cryo, thermal, chemical, immunotherapy, or combinations of these).

Whether the patient and the CBCT images are registered because the sensor 94 did not move following the imaging (step 216), or by use of the survey (step 218), this registration using a CBCT image should essentially eliminate any CT-to-body divergence issue as the CBCT images were acquired with the patient in exactly the same position as when the navigation procedure commences. Moreover, the CBCT images are taken while the patient is undergoing tidal breathing as opposed to full breath hold, thus the differences between the patient's lungs and the 3D modeling when tradition CT images are used while the patient is at full breath hold.

Though not described in detail here, the positioning and navigation of the EM sensor 94 (e.g., on bronchoscope 50, catheter 96, or other tools) may be done manually as described above in connection with catheter guide assembly 90 or may be achieved using a robotically driven catheter guide assembly.

A further method 300 that may be used with system 100 is described in connection with FIG. 3. In the method 300 a CT image and/or a CT 3D model is received and stored in a memory associated with computing device 80 at step 302. This is a standard pre-operative CT image taken with traditional CT imaging systems while the patient is at full breath hold, as described above. This pre-operative CT image is processed by the application 81 and a pathway is generated to targets within the luminal networks which have been imaged (e.g., the airways of the lungs) at step 304. Steps 302 and 304 achieve the planning phase.

At optional step 306, which may be at any time following completion of the planning phase, the patient is situated on the table 40 and the data from an survey (e.g., insertion of an EM sensor 94 into the airways) is received by the tracking system 70 and processed by application 81 in computing device 80. At step 308 CBCT image is acquired by application 81 of the desired portion of the patient using radiographic imaging device 20. This CBCT image may include the bronchoscope 50 or another device including EM sensor 94. Optionally, at step 310 a CBCT 3D model may be generated from the CBCT image. Alternatively, the acquired CBCT image received at step 308 may include a 3D model that was generated by software resident on the radio graphic imaging device 20, or on the PACS server, and supplied to the computing device 80 and application 81 with the CBCT image.

Both the pre-operative CT image that was used for the planning phase and the CBCT image acquired in step 308 are in Digital Imaging and Communications in Medicine (DICOMM) format. The DICOMM format includes reference to the coordinate system with which the image was acquired. As a result, the application 81, at step 312 transforms the coordinate system of the pre-operative CT image with the coordinate system of the CBCT image taken by the radiographic imaging device 20. Step 312 effectively registers the pre-operative CT image with the CBCT image.

Alternatively, at step 311 the application 81 aligns the CBCT 3D model generated at step 310 a 3D model generated from the pre-operative CT image and received at step 302. The alignment of the two 3D models registers the pre-operative CT image with the CBCT image. The application may present either or both of the pre-operative CT 3D model and the CBCT 3D model on a user interface and request confirmation of alignment by a user or allow for interaction by the user to finalize the orientation of the two 3D models relative to each other to finalize the registration of the two 3D models. Alternatively, this may be automatically performed by application 81.

A further alternative with respect to registration is to make an assumption as to alignment of the patient in the pre-operative CT image and the CBCT image. This process relies on the fact that during imaging with the radiographic imaging device 20 the patient is always lying flat on the table 40 with their chest away from the table 40 along the length of the table 40 and that they will be in essentially this position during the acquisition of the pre-operative CT. In this registration process, the application 81 may request via the user interface that the clinician identify a common point in both the pre-operative CT and the CBCT image. This point could be the target, as described above with respect to method 200, or it could be a point such as a main carina of the lungs or a rib or some other feature which appears in both image data sets. Alternatively, the application 81 may utilize various image processing techniques to identify these common features in the two image data sets and to register them to one another. Once identified, either manually or automatically, because of the assumption that the patient is aligned on the table 40 essentially in the same position in both images, the two image data sets (e.g., pre-operative CT and CBCT images) are registered to one another. As will be appreciated, the identification of 2, 3, 4, 5, 10 points, either automatically or by a clinician using the user interface will refine the registration even more, where desired. In some aspects this may be achieved using mutual information techniques of image brightness matching. This may be assisted by various deep learning methodologies where empirical algorithms are developed by the processing of hundreds or thousands or more images and performing the registration.

At step 314, once the two CT images or 3D models are registered to one another, all the planning data that was generated using the pre-operative CT image can be transferred to the CBCT image acquired at step 308 or to the 3D model acquired at step 310. With features such as the target and a pathway to the target, among others, transferred from the pre-operative CT image to the CBCT image, if a 3D model of the CBCT image was not generated at step 310, it can now be generated at step 316 and will include the target and pathway that has been transferred from the pre-operative CT image to the CBCT image at step 312. Alternatively, where the CBCT 3D model was generated at step 310, but the pre-operative CT 3D model and the CBCT 3D model were not registered to one another at step 311, the features transferred can be matched to the CBCT 3D model at optional step 318. Regardless of when the transfer to the features occurs, the application 81 can cause a user interface to display the CBCT 3D model and CBCT images and the features from the planning phase identified in the pre-operative CT image can be displayed therein on a user interface at step 320.

In instances where a survey was not undertaken at step 306, a survey can be undertaken at step 322. This survey registers the CBCT image and the CBCT 3D model to the patient's lungs by navigating the sensor 94, which is embodied on the bronchoscope 50, catheter 96 or another tool, into the airways of the patient, generating the point cloud discussed above. As will be appreciated, other methods of registration may also be employed without departing from the scope of the present disclosure. If the survey were conducted in step 306, above, the application may proceed during the acquisition of the CBCT image at step 308 to conduct the EM sensor 94 movement analysis, described above in step 216 to register the patient's airways to the CBCT image and 3D model generated therefrom. Once registered the detected position of the EM sensor can be used to follow a pathway in the CBCT 3D model to the target originally identified in the pre-operative CT image. The detected position of the EM sensor 94 relative to the pathway and the target is continually updated on the user interface at step 324 until the application 81 determines that the target has been arrived at step 326 and a procedure may be undertaken upon arrival at step 328. As an alternative, to use of an EM sensor 94 and detection of its position, the radiographic imaging device 20 may be capable of generating fluoroscopic images. The position of the catheter 96 may be detected in one or more fluoroscopic images that are acquired by the radio graphic imaging device 20. This detection may be manual by the clinician using a user interface on computing device 80 or may be performed by the application 81 via image processing techniques. Because the coordinate system is the same between the CBCT images and the fluoroscopic images acquired by the same device, the detected position of the catheter 96 in the fluoroscopic images can be transferred to the CBCT images or CBCT 3D model. The fluoroscopic images may be acquired periodically as the catheter 96 is navigated towards the target. The procedure may be a biopsy or a treatment of the target such as ablation (e.g., RF, microwave, cryo, thermal, chemical, immunotherapy, or combinations of these).

Figure 3:
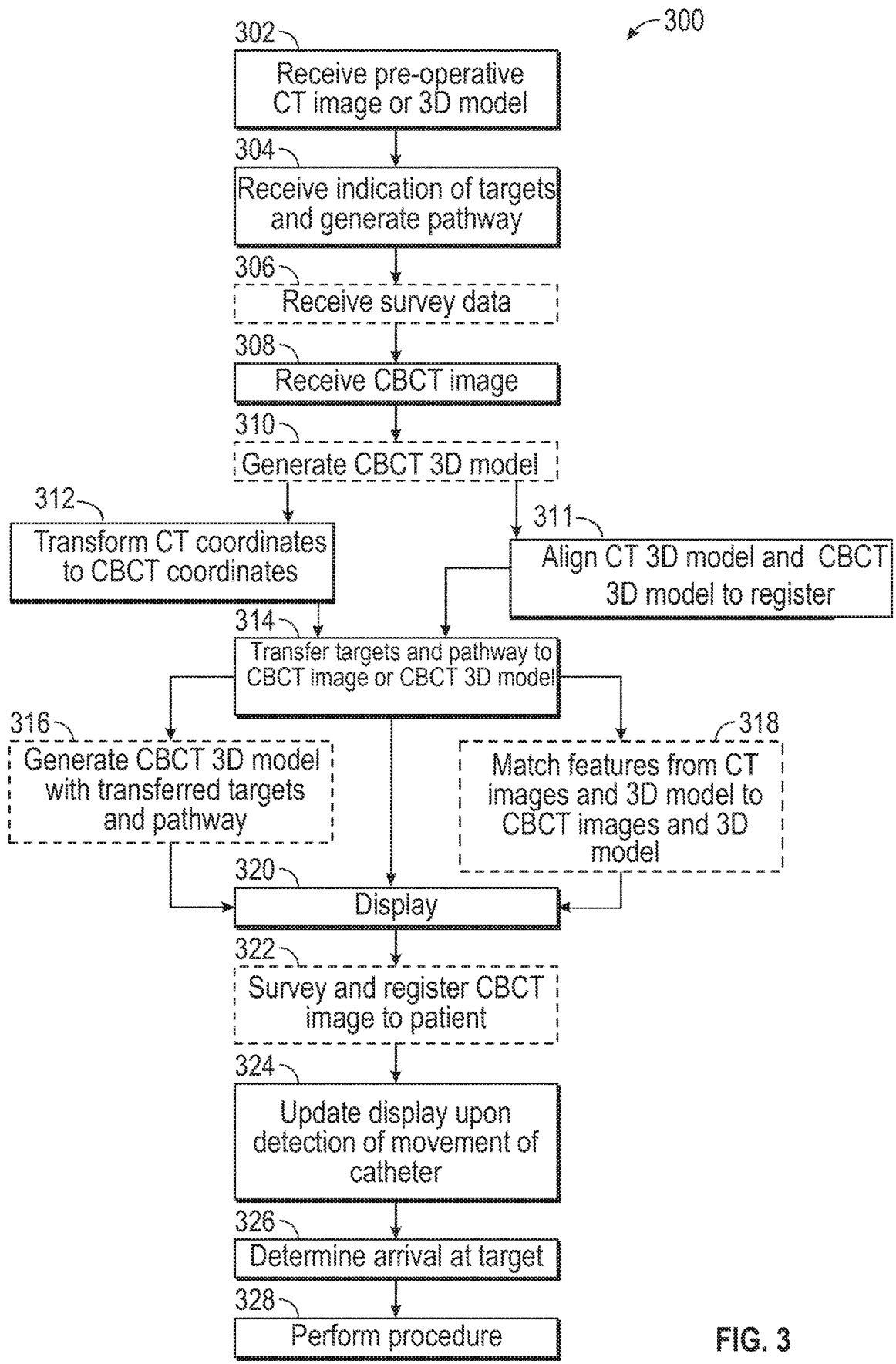
FIG. 3 is a flow chart of an imaging and navigation procedure in accordance with aspects of the disclosure.

As with the method of FIG. 2, the method of FIG. 3, eliminates the CT-to-body divergence because the CBCT image and model are generated with the patient in the same position they are in for the navigation procedure. Further the target and pathways are shown in the CBCT 3D model and CBCT images. Further, any discrepancies in registration are minimized either by the DICOMM registration process, the acquisition of the CBCT image with the sensor 94 in the image, and/or receiving survey data and matching it to the airways of the CBCT images and CBCT 3D model.

Figure 4A:
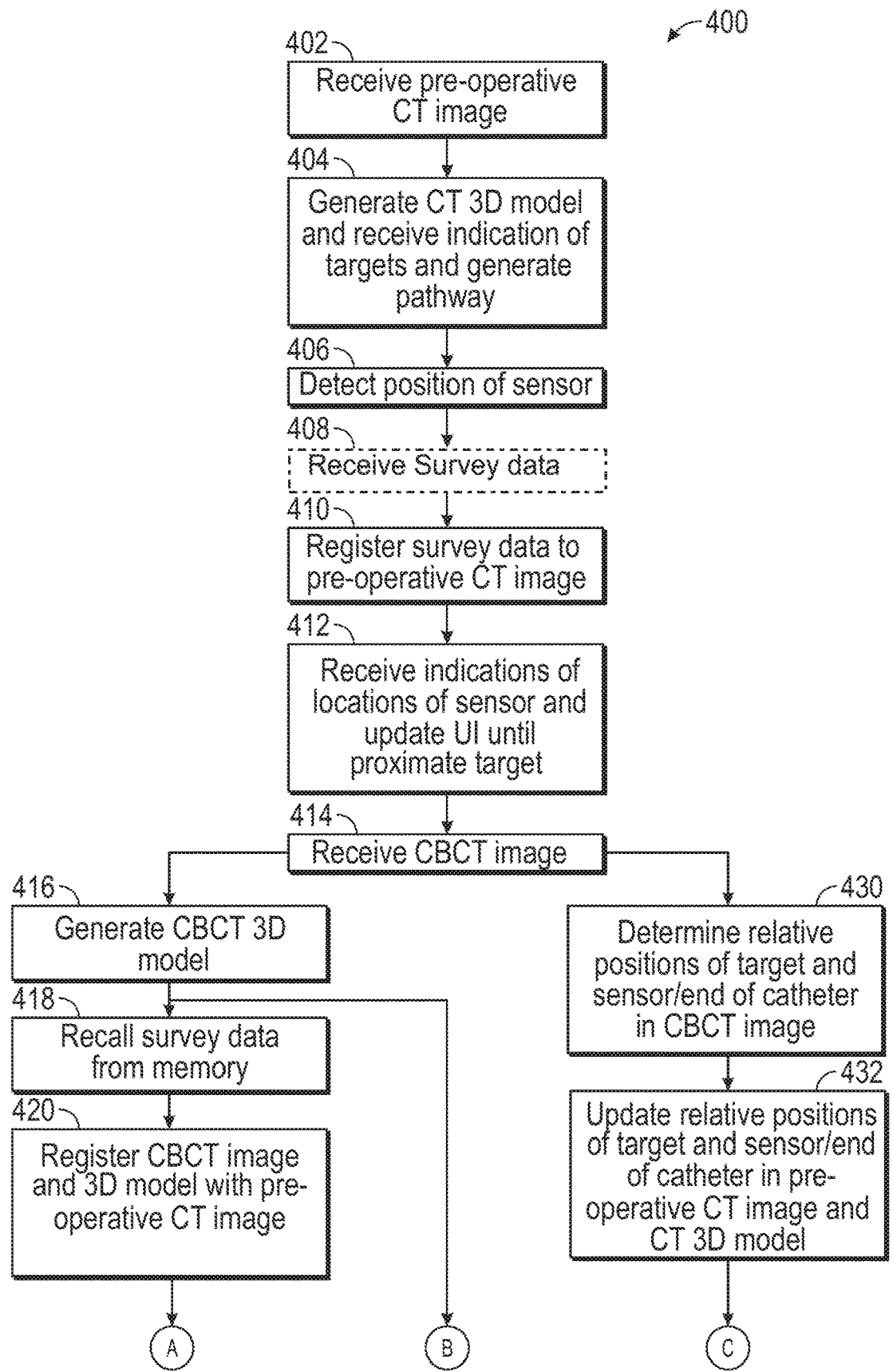
FIG. 4A is a partial flow chart of an imaging and navigation procedure in accordance with aspects of the disclosure.
Figure 4B:
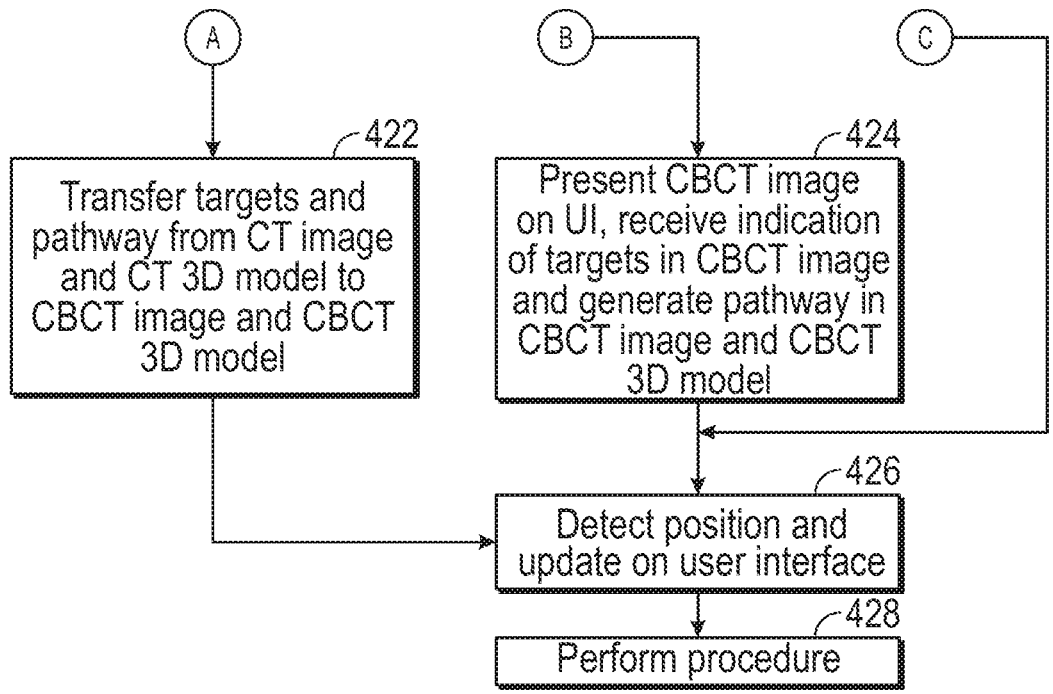
FIG. 4B is a partial flow chart of an imaging and navigation procedure in accordance with aspects of the disclosure.

A method 400 is described with reference to FIGS. 4A and 4B. In accordance with method 400, a pre-operative CT image is acquired at step 402 and saved in a memory of computing device 80. At step 404 the application 81 processes the CT image, generates a 3D model, presents on a user interface CT images on which to receive an indication of a target, and generates a pathway through the airways of a patient (or another luminal network) to reach the target. These steps complete the planning phase using a pre-operative CT image.

After the planning phase is complete, the patient may be placed on the table 40 and a bronchoscope 50 or catheter 96 inserted such that a sensor 94 can be detected by the tracking system 70 and that data provided to the application 81 at step 406. Next a survey can be conducted and a point cloud of positions of the sensor 94 received by the tracking system 70 as the survey is conducted at step 408. With the point cloud, the patient and the pre-operative CT image as well as the 3D model generated therefrom are registered to one another at step 410. As noted above, the sensor 94 may be an EM sensor, a flex sensor, or other sensor useable to determine a position of the catheter 96 or bronchoscope in a patient and depict that position in the pre-operative, thus registering the patient and the pre-operative CT image and 3D model.

With the patient and the pre-operative CT image registered navigation can commence with the tracking system 70 receiving indications of new locations of the sensor 94 as it is moved through the airways of the patient and the detected positions being updated on a user interface at step 412 as the pathway is followed to an identified target.

Once the sensor 94, and more particularly the bronchoscope 50, catheter 96, or other tool including the sensor 94, is proximate the target a CBCT image can be generated with radiographic imaging device 20 at step 414. At this point at least two different options are available. In accordance with one option, at step 416, a CBCT 3D model is generated from the CBCT image. Next at step 418 the point cloud that was generated by the survey at step 408 may be recalled from a memory in the computerized device 80 in which it is stored, and fit to the CBCT image, and the CBCT 3D model. Alternatively, the method may skip forward to step 420, where the CBCT model and the CBCT images are registered by any of the methods described herein and can be presented on a user interface. Because the CBCT image and 3D model are registered with the patient based on the survey from step 408, the pathway and targets identified at step 404 can be transferred from the pre-operative CT image 3D model to the CBCT image and CBCT 3D model at step 422 in FIG. 4B. Alternatively, in FIG. 4B the CBCT image and CBCT 3D model may be presented on the user interface at step 424 such that the target can be identified in the CBCT images. Once identification of the target is received by the application, the application generates a pathway from the location of the sensor 94, as depicted in the CBCT images and CBCT model to the target. Again, because the CBCT image is generated about the patient while they are in position on the table 40 on which the navigation is being undertaken, there is no CT-to-body divergence. The result is that the "last mile" of navigation to the target (e.g., the final 3 mm to a target) can be undertaken with heightened confidence that the target will be properly reached for biopsy or treatment. Subsequent movement of the sensor 94 is detected at step 426 and the position of the sensor 94 in the CT 3D model can be updated and a procedure can be undertaken at step 428.

As noted above, after step 414 an alternative method can be followed. At a step 430 the CBCT image, which includes the bronchoscope 50 or catheter 96 (or other tool) with sensor 94 therein is within the CBCT image, the CBCT image and/or CBCT 3D model can be analyzed to determine the relative position of the target and a distal end of the bronchoscope 50 or catheter 96. This relative position determination can be automatically derived by the application 81. Alternatively, the relative position can be determined by receipt of an indication of the location of the bronchoscope 50 or catheter 96 via the user interface, where one or more of the target and the distal end of the bronchoscope 50 or catheter 96 are shown in 2D images or the 3D model. The position of the target can be assumed to be the same in both the pre-operative CT image and the CBCT image. The relative position data can then be used by the application 81 at step 432 to update the detected position of the sensor 94 in the pre-operative CT image and the 3D model derived from the pre-operative CT. This update of position will account for the CT-to-body divergence that results from the use of the pre-operative CT image and the 3D model for navigation. Again, the last mile movement of the sensor 94 to the target can be detected at step 426 and a procedure can be performed at step 428.

Figure 5:
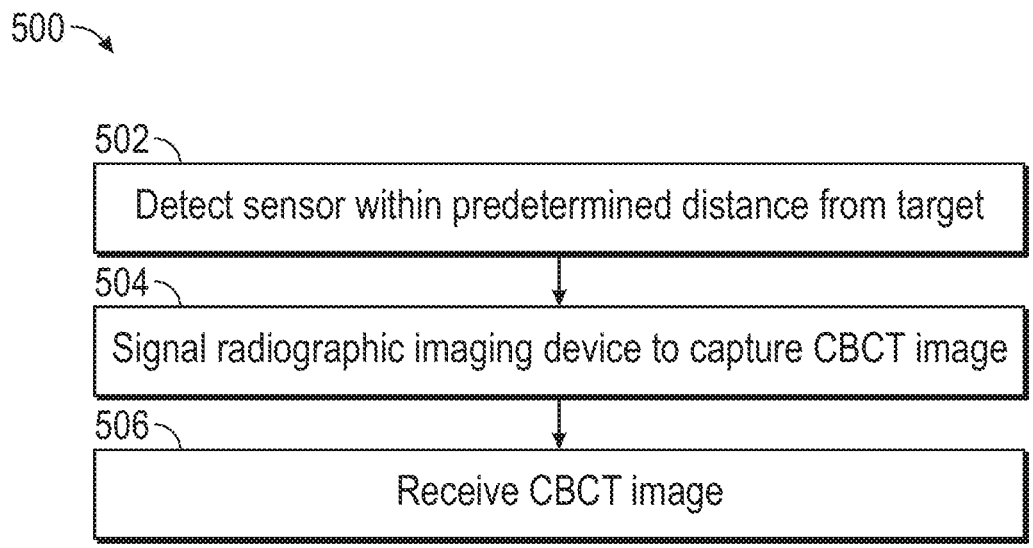
FIG. 5 is a flow chart of an imaging and navigation procedure in accordance with aspects of the disclosure.

As will be appreciated, the system 100, and particularly application 81 being run on computing device 80, can be configured to control operation of the radiographic imaging device 20. This control may be via user input to a user interface. As such according to this Alternatively, the application, can be configured, following registration of the pre-operative CT or an initial CBCT image to a patient (if required) and the identification of target, to adjust the imaging field of the CBCT to focus on the target. The application 81 may, using the location of the target in the patient, focus all future CBCT imaging on the target. This may be done without any intervention by the user. Similarly, the application 81 may initiate CBCT imaging at points during any of the methods described with respect to methods 200-400, without interaction from a user. For example in connection with a method 500 depicted in FIG. 5, as a bronchoscope 50, catheter 96, or any other tool including sensor 94 is navigated to and detected within a pre-determined distance from a target at step 502, the application 81 signals the radiographic imaging device 20 to initiate a CBCT image acquisition process at step 504. Alerts may be provided to the clinicians and surgical staff allowing them to move away from the patient and limit their exposure to the radiation emitted by the radiographic imaging device 20. These alerts may be audible or visual via the user interface.

The CBCT image is acquired via radiographic imaging device 20 and received by application 81 at step 506. This CBCT image may be used as described particularly with respect to the CBCT imaging described in the method 400. Alternatively, the use of CBCT imaging may be reviewed and considered completely separate from methods 200-400 and simply as another visual tool employed by the clinician to confirm placement, locations, and other clinical observations.

Figure 6:
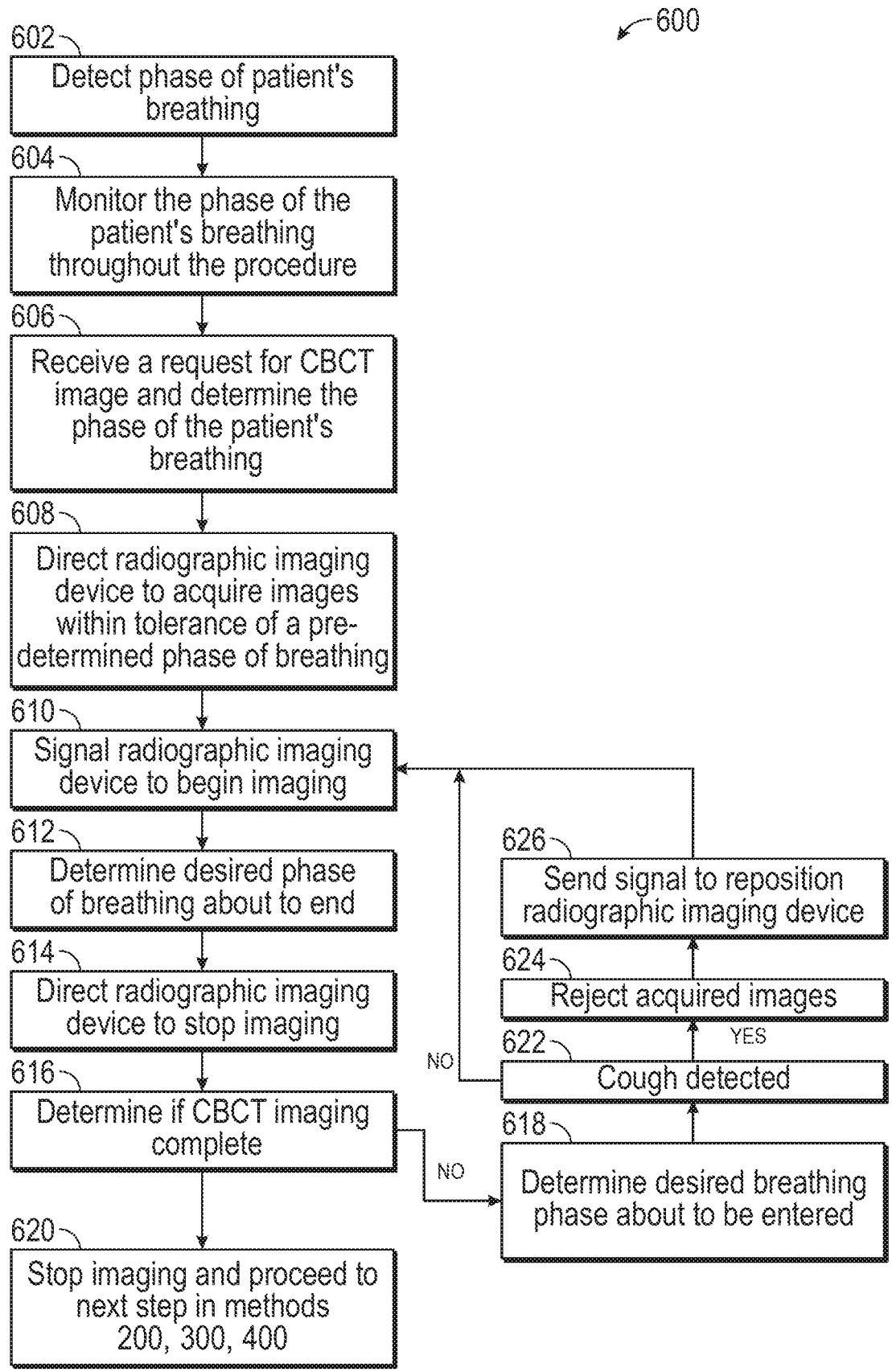
FIG. 6 is a flow chart of an imaging and navigation procedure in accordance with aspects of the disclosure.

A further aspect of the disclosure is directed to breathing detection to assist in CBCT imaging. The method 600 is described with respect to FIG. 6. Employing the output from reference sensors 74, tracking system 70 and therewith application 81 can detect the phase of the phase of the patient's breathing at step 602. This phase can be monitored throughout a procedure at step 604. Whenever a request for a CBCT image is received (either directly or via an automatic process) the application 81 can determine the phase of the patient's breathing at step 606. There are a variety of options for the application at this point depending on which method 200-400 in which the system 100 is engaged.

If the CBCT image is the first CT image acquired for a procedure, the application 81 can at step 608 direct the radiographic imaging device to only acquire images when the reference sensors are within a tolerance of a desired portion of the breathing phase (e.g., nearing end of exhale phase, or nearing end of inhale phase). For example, nearing the end of the inhale phase may allow for the airways to be in an expanded state resulting in potentially cleaner images that can generate a more accurate 3D model due to the contrast of the airways that results from airways being expanded. Alternatively, when the breathing phase is approaching the end of the exhale phase, there may be a longer duration of the breathing cycle where there is substantially no movement of the lungs, thus allowing for more images to be captured and enhancing the stability of the images as they are acquired in the CBCT image.

At step 610 the application 81 signals the radiographic imaging device 20 to being imaging. When application 81 determines at step 612 that the desired portion of breathing phase is about to end the application signals the radiographic imaging device 20 to stop imaging the patient at step 614. At step 616 the application can determine whether the CBCT imaging is complete. If not, the method continues to step 618 where the application 81 determines that the desired breathing phase is about to be entered, by monitoring the position of the reference sensors 74, and the method returns to step 610 where the radiographic imaging device 20 again acquires images during the desired portion of the breathing phase. If the CBCT imaging is complete at step 616, then the application 81 stops the radiographic imaging device 20 at step 6192 and proceeds to the next steps in methods 200-400.

Where a registration is desired between a either a pre-operative CT image or a previously acquired CBCT image, the application 81 can at step 608 signal the radiographic imaging device 20 to acquire images only during those portions of the breathing cycle that most closely match the breathing cycle of the previously acquired CT or CBCT images. By matching the breathing cycles as closely as possible, the two image data sets will more closely resemble one another making registration between the two easier and to transfer features such as a target or a pathway from the first CT image to a second. For example, in instances where registration to a pre-operative CT image is desired, the radiographic imaging device 20, can be directed by the application 81 to acquire CBCT images only during portions of the breathing cycle approaching the maximum inhale of normal tidal breathing position. When it is two CBCT images that are to be acquired the application 81 can store in memory the breathing phase of the first CBCT image and direct the radiographic imaging device 20 acquire images at the same phase of breathing at step 608.

As will be appreciated, by limiting imaging to a specified portion of the breathing phase the time required to acquire a CBCT image may be increased and may take several breathing cycles to complete. This may minimally extend the time required to acquire the CBCT image but results in greater fidelity of the captured image as the lungs are always imaged in about the same position of the breathing cycle. In addition, by monitoring the reference sensors 74, if a patient were to cough or move on the table 40 during the imaging process, the application 81 which is monitoring the positions of the reference sensors 74 thorough the breathing cycle can detect the rapid movement of the sensor 74. If such a movement is detected during imaging by the radiographic imaging device 20 at step 622, the application 81 can reject the most recently acquired portion of the CBCT image at step 624. The application 81 can then direct the radiographic imaging device 20 to reposition itself at step 626 to reacquire a portion of the CBCT image that corresponds to that which was rejected in the next breathing phase and the method proceeds back to step 610.

Figure 7:
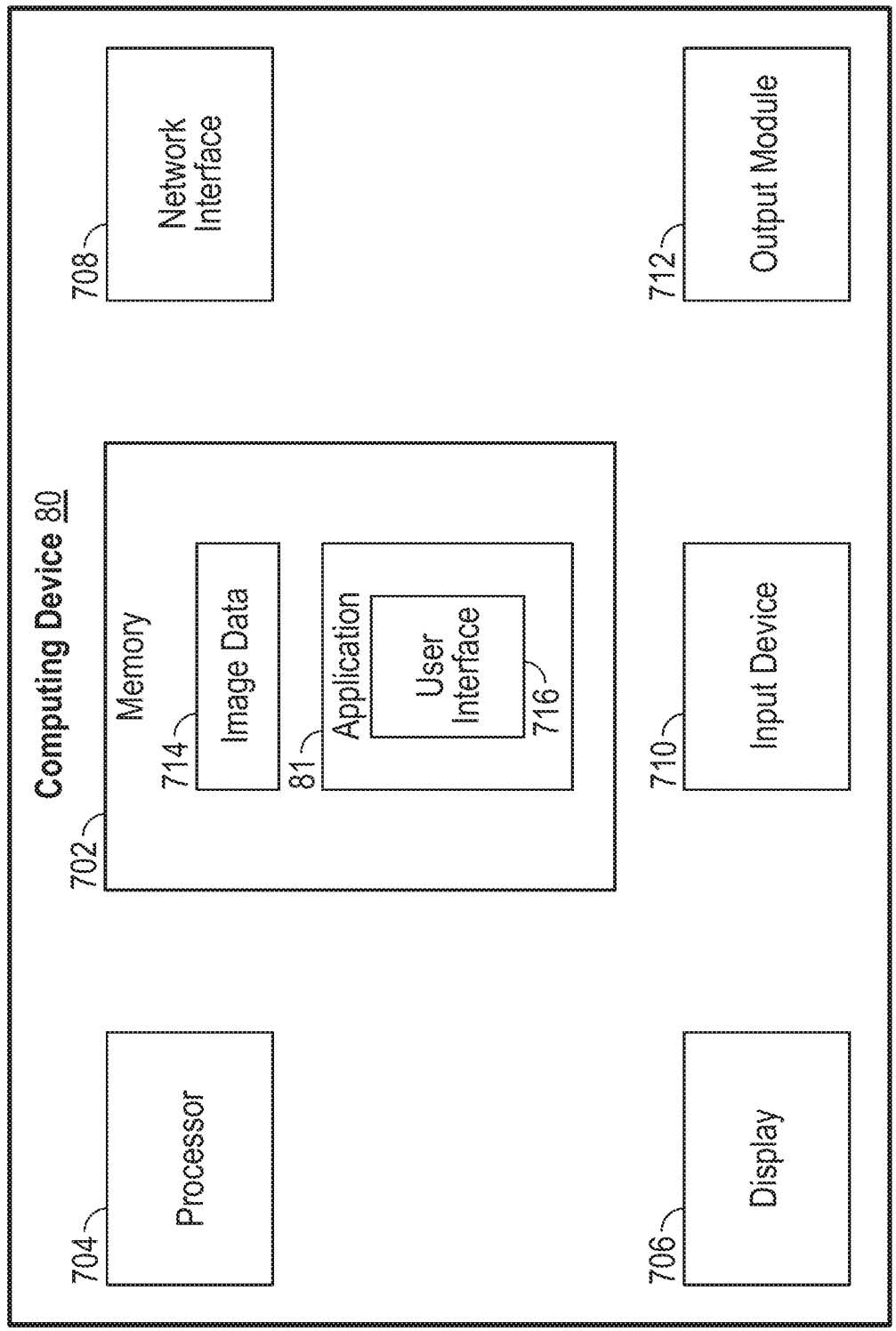
FIG. 7 is a block diagram depicting features and components of a computing device in accordance with aspects of the disclosure.

Turning now to FIG. 7, there is shown a simplified block diagram of computing device 80. Computing device 80 may include a memory 702, a processor 704, a display 706, a network interface 708, an input device 710, and/or an output module 712. Memory 702 may store application 81 and/or image data 514. Application 81 may, when executed by processor 704, cause display 706 to present user interface 716. Application 81 may also provide the interface between the sensed position of EM sensor 94 and the image and planning data developed in the pathway planning phase, described above.

Memory 702 may include any non-transitory computer-readable storage media for storing data and/or software that is executable by processor 704 and which controls the operation of computing device 80. In an embodiment, memory 507 may include one or more solid-state storage devices such as flash memory chips. Alternatively, or in addition to the one or more solid-state storage devices, memory 702 may include one or more mass storage devices connected to the processor 704 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 704. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Network interface 708 may be configured to connect to a network such as a local area network (LAN) consisting of a wired network and/or a wireless network, a wide area network (WAN), a wireless mobile network, a Bluetooth network, and/or the internet. Input device 710 may be any device by means of which a user may interact with computing device 80, such as, for example, a mouse, keyboard, foot pedal, touch screen, and/or voice interface. Output module 712 may include any connectivity port or bus, such as, for example, parallel ports, serial ports, universal serial busses (USB), or any other similar connectivity port known to those skilled in the art.

Figure 8:
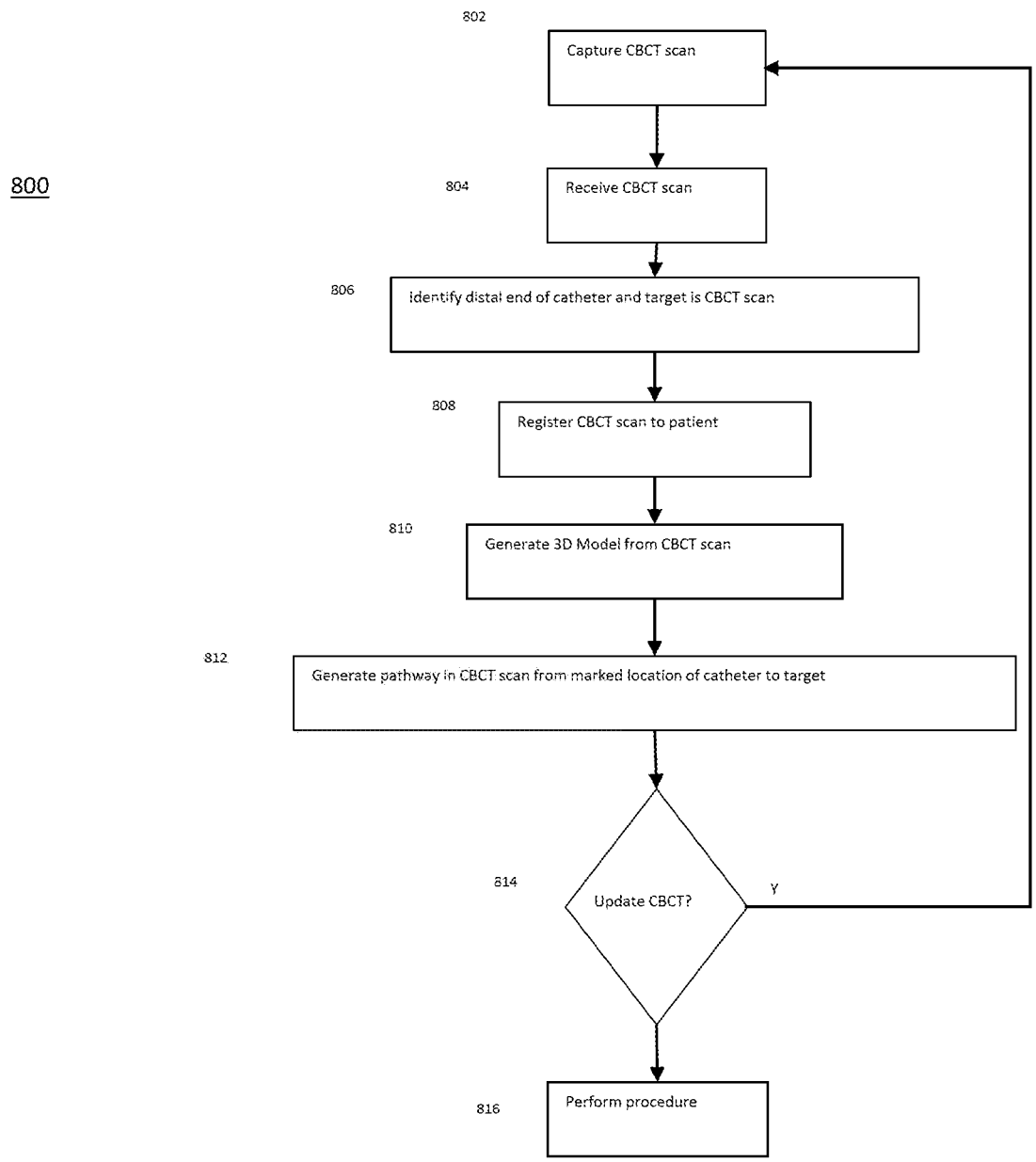
FIG. 8 is a flow chart of an imaging and navigation procedure in accordance with aspects of the disclosure.

FIG. 8 describes a method 800 requiring no pre-procedure CT scan data. In FIG. 8 method 800 follows steps of set up of the system 100, placement of the patient on the operating table 40, and initial navigation of catheter guide assembly 90 either alone or in combination with bronchoscope 50 to a location within the lungs. The location within the lungs could be a target lobe or other anatomical point. As an example, the location may be the third bifurcation in a desire lobe of the lung. Once at this location, method 800 starts with capturing a CBCT scan at step 802 using radiographic imaging device 20. The computing device 80 receives the CBCT scan at step 804. For example, the application 81 may be retrieve the CBCT scan from a database in which the scan was stored following capture, or a user may direct the radiographic imaging device 20 to output the CBCT scan directly to the computing device 80. At step 806, the distal end of the catheter 96 and a target (e.g., a lesion or other location for treatment) are identified in one or more images of the CBCT scan. This identification can be manual where the user marks the distal end of the catheter 96 and the target in one or more of the images of the CBCT scan. These images may be displayed in a user interface on computing device 80. Alternatively, the application 81 may be configured to conduct image analysis and to automatically identify the distal end of the catheter 96 and the target. If either or both of the distal portion of the catheter or the target cannot be identified in the CBCT images from the scan, the process can return to step 802 to conduct another CBCT scan. This may require repositioning of the patient, radiographic imaging device 20, or the catheter 96.

Following identification, at step 808 the computing device 80 can register the CBCT scan data with the electromagnetic field generated by the tracking system 70. Registration may be undertaken in a variety of ways. If, for example, the coordinate system of the radiological image device 20 is perpendicular to the operating table 40, all that is required is translation of the CBCT coordinates to match the tracking system (e.g., EM coordinates of the field produced by EM field generator 76). Alternatively, registration may be achieved utilizing a pose estimation technique.

To determine the pose for each slice making up the CBCT scan, fiducial markers which are formed in or on the EM field generator 76 placed under the patient are analyzed. The markers may be evenly spaced or may be varyingly spaced from one another in a known pattern. Regardless of how spaced, the orientation and placement of the markers is know and the spacing and positioning of the markers in any slice of the CBCT can be analyzed to determine the angle of the device relative to the radiographic imaging device 20 relative to the EM field generator 76. With the known position of the markers, and both a marked position of the distal portion of the catheter 96 and a detected position of the catheter as identified by the tracking system 70, a mathematical transform from the coordinate system of the CBCT scan data to the coordinate system of the tracking system 70 (e.g., EM coordinates).

Once registration is complete, at step 810, a 3D model of the patient's lungs can be generated from the CBCT scan, similar to the process described above with the pre-procedure CT image. At step 312, a pathway is generated through the 3D model from the marked position of the distal portion of the catheter 96 to the marked position of the target. This pathway may be manually created by a user, semi-automatically, or automatically derived, much as it might be in a 3D model from a pre-procedure CT scan. Navigation to the target may now be undertaken. If at any time during the navigation the user wishes to perform another CBCT scan, the decision can be made at step 814 and the process can revert back to step 302. The use of multiple CBCT scans may be desirable, for example, when performing microwave or RF ablation procedures within the lungs to ensure accurate placement of an ablation catheter in a desired location in the target. Once navigated to an appropriate location, a user or a robot may remove the LG 92 to allow for placement of an ablation catheter or other tool (e.g., a biopsy tool) to perform a procedure at step 816.

Figure 9:
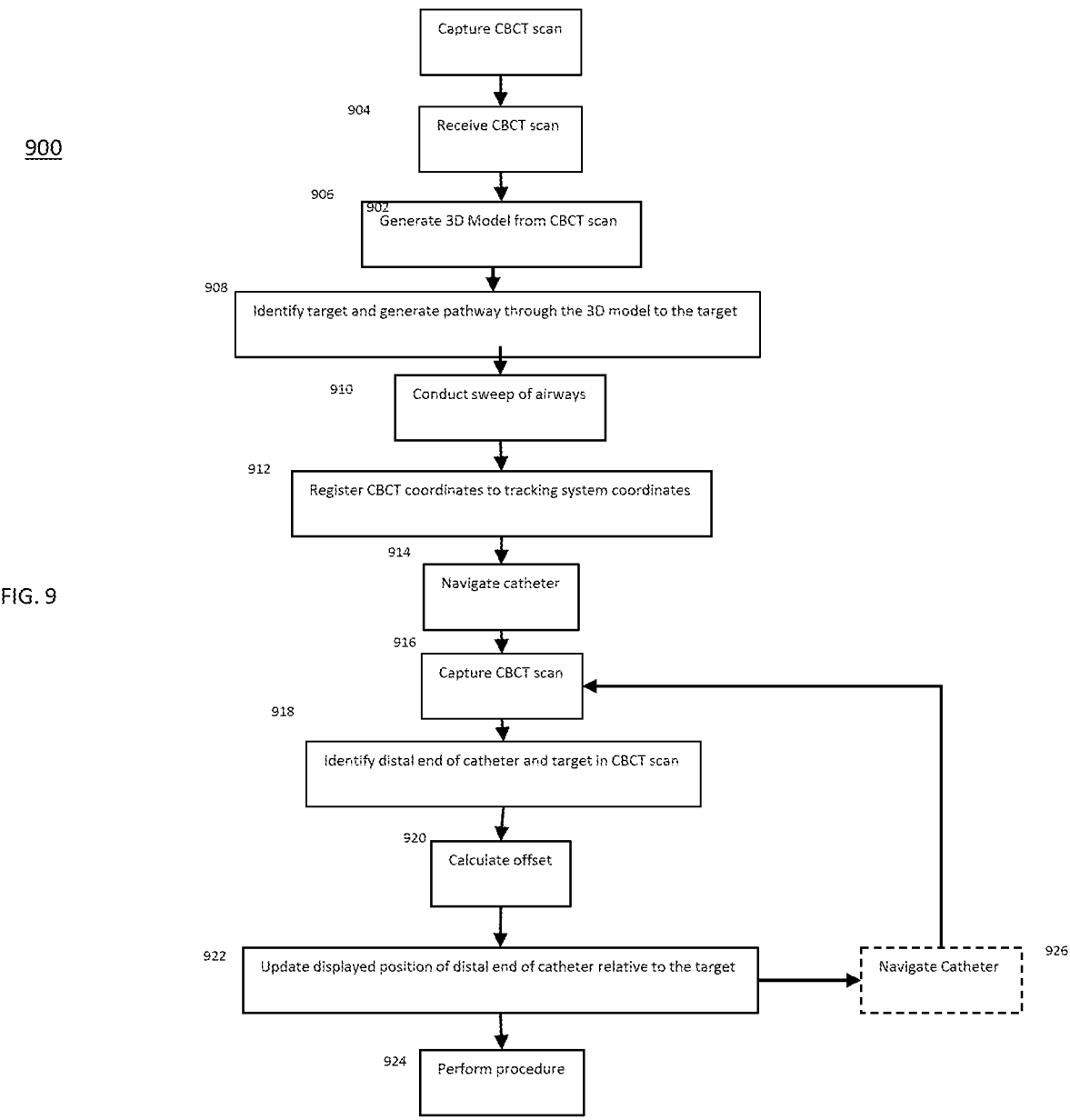
FIG. 9 is a flow chart of an imaging and navigation procedure in accordance with aspects of the disclosure.

FIG. 9 depicts a method 900 requiring no pre-procedure CT scan data. As with method 800, method 900 follows steps of set up of the system 100 and placement of the patient on the operating table 40. Rather than initiate navigation as described in method 800, at step 902 a CBCT scan of the patient is undertaken. The computing device 80 receives the CBCT scan at step 904. For example, the application 81 may be retrieve the CBCT scan from a database in which the scan was stored following capture, or a user may direct the radiographic imaging device 20 to output the CBCT scan directly to the computing device 80. At step 906 a 3D model of the airways is generated from the CBCT scan. At step 908 either the 3D model, or slice images from the CBCT image are analyzed to identify a target (e.g., a lesion) and to generate a pathway to the target through the airway in the same manner as can be done with a pre-procedure CT image. Following target identification and pathway planning, a sweep of the airways may be undertaken at step 910. As described above, in the sweep of the airways, sensor 94 of catheter 96 is inserted into the airways and a point cloud of position data is generated. At step 912, the point cloud of data is matched to the internal features of the 3D model and the coordinate system of radiographic imaging device 20 is registered to the electromagnetic field coordinate system of the EM field output by the EM field generator 76. Once registered navigation of the catheter 96, either manually or robotically can be undertaken at step 914. Once proximate a target, a second CBCT scan may be undertaken at step 916. Reviewing the slice images of the CBCT scan, at step 918 the positions of the distal end of the catheter 96 and the target can be marked. At step 920, based on the marked positions of the distal portion of the catheter 96 and the target and offset can be calculated. Since the position of the target is unlikely to have moved significantly during the procedure, this offset is substantially and indication of error in the detected position of the sensor 94 at the distal end of the catheter 96 in the EM filed. With this offset calculated, at step 922 a displayed position of the distal portion of the catheter 96 in the 3D model can be updated to accurately depict the relative position of the catheter and the target in the 3D model, and in other views provided by the user interface of application 81 described herein above. The combination of steps 920 and 922 are a local registration of the CBCT and the EM field coordinate systems and again provide greater accuracy as may be desired when performing a procedure at step 924 such as microwave ablation or diagnostics such as biopsy of a lesion. If further movement of the catheter is desired further navigation can be undertaken at step 926, and the method can revert back to step 916 to update the local registration.

Figure 10:
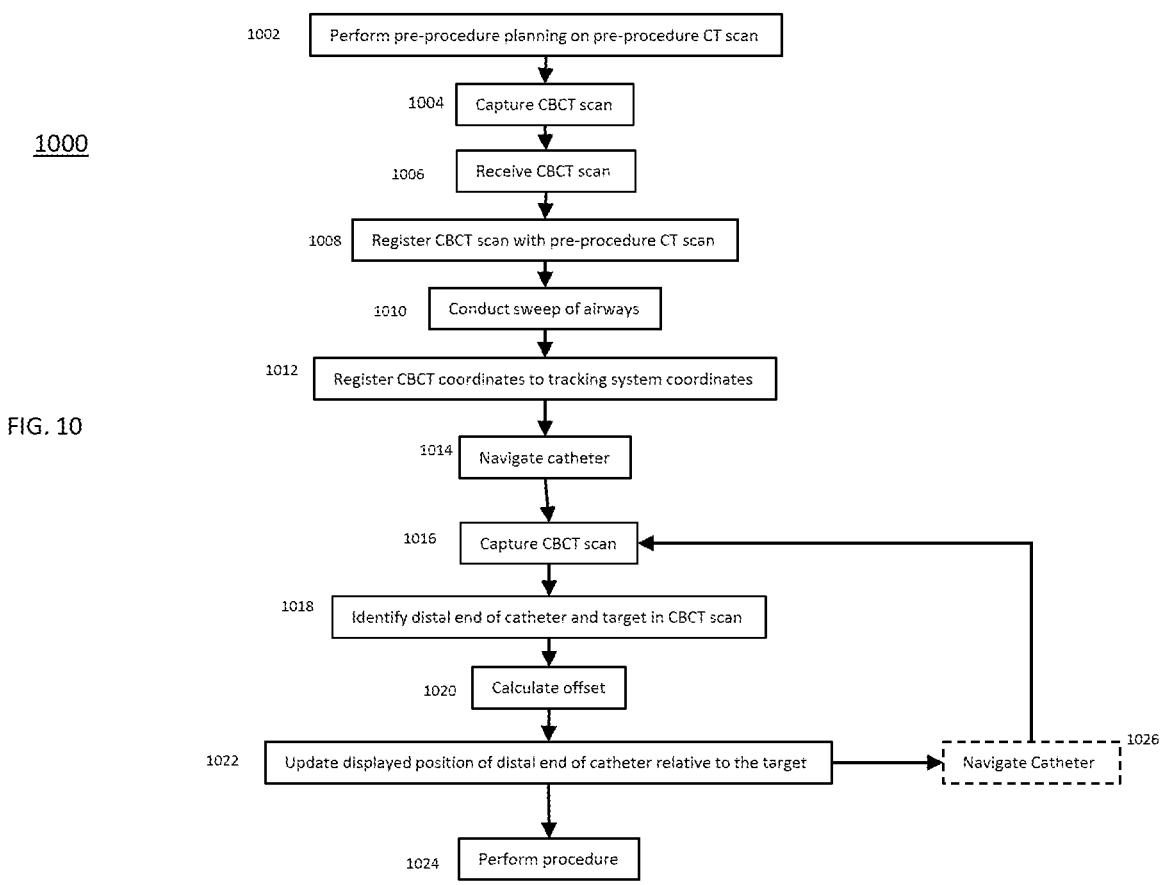
FIG. 10 is a flow chart of an imaging and navigation procedure in accordance with aspects of the disclosure.

FIG. 10 provides yet a further method in accordance with the disclosure. In method 1000, at step 1002 pre-procedure planning (as described above) is undertaken utilizing a pre-procedure CT scan. At some time after the pre-procedure planning, system 100 is initialized, this may entail placement of the patient on the operating table 40 and initializing of the tracking system 70 and other steps described above. Once the patient is in position, at step 1004 the radiological imaging device 20 is employed to acquire a CBCT scan of a relevant portion of the patient (e.g., the lungs). At step 1006, the application 81 operating on computing device 80 receives the CBCT scan. For example, the application 81 may be retrieve the CBCT scan from a database in which the CBCT scan was stored following capture, or a user may direct the radiographic imaging device 20 to output the CBCT scan directly to the computing device 80. At step 1008 the CBCT scan is registered to the pre-operative scan. A variety of means can be used for this registration, for example image or 3D model matching may be employed to substantially match the pre-procedure CT scan to the CBCT scan. This registration enables the transfer of a planned pathway and a target from the pre-procedure plan generated from the pre-procedure CT scan to the CBCT scan. As a result of this registration, a user interface on the computing device 80 can display a pathway through a 3D model and other views generated from the CBCT scan to the target which is also now presented in the CBCT scan images. At step 1010, a sweep of the airways may be undertaken. As described above, in the sweep of the airways, sensor 94 of catheter 96 is inserted into the airways and a point cloud of position data is generated. At step 1012, the point cloud of data is matched to the internal features of the 3D model generated from the CBCT scan and the coordinate system of radiographic imaging device 20 is registered to the electromagnetic field coordinate system of the EM field output by the EM field generator 76 (or other tracking system 70 described herein). Once registered navigation of the catheter 96, either manually or robotically can be undertaken at step 1014. Once proximate a target, a second CBCT scan may be undertaken at step 1016. Reviewing slice images of the CBCT scan, at step 1018 the positions of the distal end of the catheter 96 and the target can be marked. At step 1020, based on the marked positions of the distal portion of the catheter 96 and the target and offset can be calculated. This offset is used to update the detected position of the sensor 94 in the EM field relative to the target. With this offset calculated, at step 1022 a displayed position of the distal portion of the catheter 96 in the 3D model generated from the CBCT scan can be updated to accurately depict the relative position of the catheter and the target in the 3D model, as well as other views provided by the user interface of application 81 described herein above. The combination of steps 1020 and 1022 are a local registration of the CBCT and the EM field coordinate systems and again provide greater accuracy as may be desired when performing a procedure at step 1024 treatment such as microwave ablation or diagnostics such as biopsy of a lesion. If further movement of the catheter 96 is desired further navigation can be undertaken at step 1026, and the method can revert back to step 1016 to update the local registration.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects.

What is claimed is:

1. A method of registering an image to a luminal network comprising:
   detecting a position of a catheter-based sensor within a luminal network;
   receiving cone-beam computed tomography (CBCT) images of the luminal network with the sensor within the luminal network;
   presenting a CBCT image on a user interface;
   receiving an indication of a location of a target in the presented CBCT image;
   generating a 3D model of the luminal network from the CBCT images;
   generating a pathway through the luminal network from the detected position of the sensor to the target in the CBCT images and the 3D model; and
   comparing a detected position of the catheter-based sensor in the luminal network prior to receiving the CBCT images to a detected position of the catheter-based sensor in the luminal network after receiving the CBCT images, wherein when it is determined that the detected position of the catheter-based sensor prior to the receipt of the CBCT images is substantially the same as the detected position of the catheter-based sensor after receipt of the CBCT images, the luminal network, the CBCT images, and the 3D model are registered.

2. The method of claim 1, further comprising receiving survey data from the catheter-based sensor when it is determined that the detected position of the sensor after receipt of the CBCT images is different from the detected position of the sensor prior to receipt of the CBCT images.

3. The method of claim 2, further comprising registering the luminal network to the CBCT images based on survey data.

4. The method of claim 1, further comprising displaying the pathway in the CBCT images, the 3D model generated from the CBCT images, or a virtual bronchoscopy view of the 3D model from the CBCT images.

5. The method of claim 4 further comprising displaying the position of the sensor along the pathway in the user interface.

6. A method of registering an image to a luminal network comprising:
- receiving a pre-operative computed tomography (CT) image of the luminal network;
- receiving an indication of a target within the luminal network in the CT image;
- generating a pathway through the luminal network to the target;
- receiving cone-beam computed tomography (CBCT) images of the luminal network;
- detecting a location of a catheter-based sensor within the luminal network;
- generating a 3D model of the luminal network from the CBCT images;
- transforming coordinates of the pre-operative CT image to coordinates of the CBCT images to register the pre-operative CT image to the CBCT images;
- matching features from the CT images to features of the CBCT images and 3D model derived from the CBCT images; and
- displaying the pathway from the detected location of the catheter-based sensor to the target in the CBCT images or 3D model.

7. The method of claim 6, further comprising displaying, the 3D model derived from the CBCT images, or a virtual bronchoscopy view of the 3D model from the CBCT images on a user interface.

8. The method of claim 6 further comprising generating the 3D model from the CBCT image before transforming the pre-operative CT coordinates and the CBCT coordinates.

9. The method of claim 6, further comprising:
- transferring the target from the pre-operative CT image to the CBCT images; and
- generating the 3D model from the CBCT images after transferring the target and pathway from the pre-operative CT image to the CBCT images.

10. The method of claim 6, further comprising receiving survey data, wherein the survey data is received prior to receipt of the CBCT images or the survey data is received after transfer of the target and pathway to the CBCT images from the pre-operative CT image to register the CBCT images to the luminal network.

* * * * *